(12) United States Patent
Søe

(10) Patent No.: US 7,781,001 B2
(45) Date of Patent: *Aug. 24, 2010

(54) FOODSTUFF

(75) Inventor: Jørn Borch Søe, Mundelstrup (DK)

(73) Assignee: Danisco A/S, Copenhagen (DK)

( * ) Notice: Subject to any disclaimer, the term of this patent is extended or adjusted under 35 U.S.C. 154(b) by 1509 days.

This patent is subject to a terminal disclaimer.

(21) Appl. No.: 10/409,391

(22) Filed: Apr. 8, 2003

(65) Prior Publication Data

US 2004/0091574 A1 May 13, 2004

Related U.S. Application Data

(60) Division of application No. 09/750,990, filed on Dec. 28, 2000, which is a continuation-in-part of application No. PCT/IB99/01354, filed on Jul. 20, 1999.

(30) Foreign Application Priority Data

| Jul. 21, 1998 | (GB) | ................................... 9815905.6 |
| Nov. 11, 1998 | (GB) | ................................... 9824758.8 |

(51) Int. Cl.
*A23L 1/23* (2006.01)

(52) U.S. Cl. .............................. 426/33; 426/18; 426/34; 426/42; 426/44; 426/47; 426/52; 426/56; 426/574; 426/601; 426/602; 426/603; 426/604; 426/605; 426/606; 426/607; 426/608; 426/609; 426/611; 426/615; 426/641

(58) Field of Classification Search .................... 426/18, 426/33, 34, 42, 44, 47, 52, 56, 574, 601, 426/602, 603, 604, 605, 606, 607, 608, 609, 426/611, 615, 641
See application file for complete search history.

(56) References Cited

U.S. PATENT DOCUMENTS

| 2,888,385 A | 5/1959 | Grandel |
| 3,260,606 A | 7/1966 | Azuma |
| 3,368,903 A | 2/1968 | Johnson et al. |
| 3,520,702 A | 7/1970 | Menzi |
| 3,634,195 A | 1/1972 | Melaschouris |
| 3,652,397 A | 3/1972 | Pardun |
| 3,677,902 A | 7/1972 | Aunstrup |
| 3,852,260 A | 12/1974 | Knutsen |
| 3,973,042 A | 8/1976 | Kosikowski |
| 4,034,124 A | 7/1977 | Van Dam |
| 4,065,580 A | 12/1977 | Feldman |
| 4,160,848 A | 7/1979 | Vidal |
| 4,202,941 A | 5/1980 | Terada |
| 4,399,218 A | 8/1983 | Gauhl |
| 4,567,046 A | 1/1986 | Inoue |
| 4,683,202 A | 7/1987 | Mullis |
| 4,689,297 A | 8/1987 | Good |
| 4,707,291 A | 11/1987 | Thom |
| 4,707,364 A | 11/1987 | Barach |
| 4,708,876 A | 11/1987 | Yokoyama et al. |
| 4,798,793 A | 1/1989 | Eigtved |
| 4,808,417 A | 2/1989 | Masuda |
| 4,810,414 A | 3/1989 | Huge-Jensen |
| 4,814,331 A | 3/1989 | Kerkenaar |
| 4,818,695 A | 4/1989 | Eigtved |
| 4,826,767 A | 5/1989 | Hansen |
| 4,865,866 A | 9/1989 | Moore |
| 4,904,483 A | 2/1990 | Christensen |
| 4,916,064 A | 4/1990 | Derez |
| 5,112,624 A | 5/1992 | Johna |
| 5,213,968 A | 5/1993 | Castle |
| 5,219,733 A | 6/1993 | Myojo |
| 5,219,744 A | 6/1993 | Kurashige |
| 5,232,846 A | 8/1993 | Takeda |
| 5,264,367 A | 11/1993 | Aalrust |
| 5,273,898 A | 12/1993 | Ishii |
| 5,288,619 A | 2/1994 | Brown et al. |
| 5,290,694 A | 3/1994 | Nakanishi |
| 5,378,623 A | 1/1995 | Hattori |
| 5,523,237 A | 6/1996 | Budtz |
| 5,536,661 A | 7/1996 | Boel |
| 5,558,781 A | 9/1996 | Buchold |
| 5,650,188 A | 7/1997 | Gaubert |
| 5,677,160 A | 10/1997 | Oester |
| 5,695,802 A * | 12/1997 | Van Den Ouweland et al. .......................... 426/533 |
| 5,716,654 A | 2/1998 | Groenendaal |
| 5,763,383 A | 6/1998 | Hashida |
| 5,766,912 A | 6/1998 | Boel |
| 5,776,741 A | 7/1998 | Pedersen |
| 5,814,501 A | 9/1998 | Becker |
| 5,821,102 A | 10/1998 | Berka |
| 5,827,719 A | 10/1998 | Sandal |
| 5,830,736 A | 11/1998 | Oxenboll |
| 5,834,280 A | 11/1998 | Oxenboll |
| 5,856,163 A | 1/1999 | Hashida |

FOREIGN PATENT DOCUMENTS

AR 249546 12/1996

(Continued)

OTHER PUBLICATIONS

Council Regulation (EC) No. 291/94of Dec. 5, 1994 "laying down standards for spreadable fats." Official Journal of the European Communities, Sep. 12, 1994, No. L316/2-7.

(Continued)

*Primary Examiner*—Leslie Wong
(74) *Attorney, Agent, or Firm*—Frommer Lawrence & Haug LLP; Thomas J. Kowalski; Smitha B. Uthaman

(57) ABSTRACT

There is provided use of a conversion agent to prepare from a food material a foodstuff comprising at least one functional ingredient, wherein the at least one functional ingredient has been generated from at least one constituent of the food material by the conversion agent.

8 Claims, 2 Drawing Sheets

U.S. PATENT DOCUMENTS

| | | |
|---|---|---|
| 5,863,759 A | 1/1999 | Boel |
| 5,869,438 A | 2/1999 | Svendsen |
| 5,874,558 A | 2/1999 | Boel |
| 5,879,920 A | 3/1999 | Dale |
| 5,892,013 A | 4/1999 | Svendsen |
| 5,914,306 A | 6/1999 | Svendsen |
| 5,916,619 A | 6/1999 | Miyazaki |
| 5,919,746 A | 7/1999 | Hirayama |
| 5,929,017 A | 7/1999 | Gormsen |
| 5,965,384 A | 10/1999 | Boel |
| 5,965,422 A | 10/1999 | Loffler |
| 5,976,855 A | 11/1999 | Svendsen |
| 5,989,599 A | 11/1999 | Chmiel |
| 5,990,069 A | 11/1999 | Andre |
| 6,001,586 A | 12/1999 | Schellenberger |
| 6,001,640 A | 12/1999 | Loeffler |
| 6,020,180 A | 2/2000 | Svendsen |
| 6,066,482 A | 5/2000 | Steffens |
| 6,074,863 A | 6/2000 | Svendsen |
| 6,103,505 A | 8/2000 | Clausen |
| 6,110,508 A | 8/2000 | Olesen |
| 6,140,094 A | 10/2000 | Loffler |
| 6,143,543 A | 11/2000 | Michelsen et al. |
| 6,143,545 A | 11/2000 | Clausen |
| 6,146,869 A | 11/2000 | Harris |
| 6,156,548 A | 12/2000 | Christensen |
| 6,180,406 B1 | 1/2001 | Stemmer |
| 6,254,645 B1 | 7/2001 | Kellis |
| 6,254,903 B1 | 7/2001 | Schuster et al. |
| 6,344,328 B1 | 2/2002 | Short |
| 6,350,604 B1 | 2/2002 | Hirayama |
| 6,358,543 B1 | 3/2002 | Soe |
| 6,361,974 B1 | 3/2002 | Short |
| 6,365,204 B1 | 4/2002 | Spendler |
| 6,432,898 B1 | 8/2002 | Rey |
| 6,495,357 B1 | 12/2002 | Fuglsang |
| 6,506,588 B2 | 1/2003 | Tsutsumi |
| 6,509,182 B2 | 1/2003 | Tsutsumi |
| 6,511,837 B2 | 1/2003 | Tsutsumi |
| 6,514,739 B1 | 2/2003 | Udagawa |
| 6,558,715 B1 | 5/2003 | Rey |
| 6,582,942 B1 | 6/2003 | Christensen |
| 6,624,129 B1 | 9/2003 | Borch |
| 6,645,749 B2 | 11/2003 | Vind |
| 6,682,922 B2 | 1/2004 | Berka |
| 6,686,189 B2 | 2/2004 | Rey |
| 6,730,346 B2 | 5/2004 | Rey |
| 6,815,190 B1 | 11/2004 | Abo |
| 6,852,346 B2 | 2/2005 | Soe |
| 6,964,944 B1 | 11/2005 | Callisen et al. |
| 2002/0098536 A1 | 7/2002 | Norinobu |
| 2002/0110854 A1 | 8/2002 | Tsutsumi |
| 2002/0142434 A1 | 10/2002 | Tsutsumi |
| 2002/0168746 A1 | 11/2002 | Tsutsumi |
| 2003/0003561 A1 | 1/2003 | Vind |
| 2003/0028923 A1 | 2/2003 | Lardizabal |
| 2003/0040450 A1 | 2/2003 | Rey |
| 2003/0074695 A1 | 4/2003 | Farese |
| 2003/0100092 A1 | 5/2003 | Berka |
| 2003/0119164 A1 | 6/2003 | Udagawa |
| 2003/0148495 A1 | 8/2003 | Hastrup |
| 2003/0180418 A1 | 9/2003 | Rey |
| 2003/0185939 A1 | 10/2003 | Nielsen |
| 2003/0215544 A1 | 11/2003 | Nielsen |
| 2004/0005399 A1 | 1/2004 | Chakrabarti |
| 2004/0235106 A1 | 11/2004 | Kapeller-Libermann |
| 2004/0235119 A1 | 11/2004 | Hoppe et al. |
| 2005/0059130 A1 | 3/2005 | Bojsen |
| 2005/0059131 A1 | 3/2005 | Bisgard-Frantzen |
| 2005/0118697 A1 | 6/2005 | Budolfsen |
| 2005/0142647 A1 | 6/2005 | Wassell |
| 2006/0075518 A1 | 4/2006 | Yaver et al. |

FOREIGN PATENT DOCUMENTS

| | | |
|---|---|---|
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 805618 | 2/1969 |
| CA | 1270781 | 6/1990 |
| CA | 2012723 | 9/1990 |
| CA | 2134597 | 10/1994 |
| CA | 2224143 | 12/1996 |
| CA | 2 403 025 | 4/2004 |
| DE | 2817087 | 11/1978 |
| DE | 19620649 | 11/1997 |
| DE | 69129988 | 3/1999 |
| DE | 69330066 | 10/2001 |
| DE | 69527835 | 4/2003 |
| DE | 69528070 | 6/2003 |
| DE | 69904161 | 7/2003 |
| DE | 69716711 | 9/2003 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |
| DK | 0543/98 | 4/1998 |
| DK | PA0543/98 | 4/1998 |
| DK | PA199801572 | 11/1998 |
| DK | PA5677000 | 12/1998 |
| DK | PA199801604 | 12/1998 |
| DK | PA199901736 | 12/1999 |
| DK | PA200000989 | 6/2000 |
| DK | PA200000991 | 6/2000 |
| DK | PA200100285 | 2/2001 |
| DK | PA200100843 | 5/2001 |
| DK | EP659049 | 6/2001 |
| DK | EP0784674 | 11/2002 |
| DK | EP0869167 | 1/2003 |
| DK | EP1073339 | 1/2003 |
| DK | PA200300634 | 4/2003 |
| DK | EP0746608 | 10/2003 |
| DK | EP1042458 | 3/2004 |
| EP | 0064855 | 11/1982 |
| EP | 0010296 | 12/1982 |
| EP | 0109244 | 5/1984 |
| EP | 0130064 | 1/1985 |
| EP | 0140542 | 5/1985 |
| EP | 0167309 | 1/1986 |
| EP | 0171995 | 2/1986 |
| EP | 0 191 217 A1 | 8/1986 |
| EP | 0205208 | 12/1986 |
| EP | 0206390 | 12/1986 |
| EP | 0214761 | 3/1987 |
| EP | 0109244 | 4/1987 |
| EP | 0257388 | 3/1988 |
| EP | 0260573 | 3/1988 |
| EP | 0334462 | 9/1989 |
| EP | 0195311 | 6/1990 |
| EP | 0375102 | 6/1990 |
| EP | 0426211 | 5/1991 |
| EP | 0 445 692 A2 | 9/1991 |
| EP | 0445692 | 9/1991 |
| EP | 0449375 | 10/1991 |
| EP | 0468731 | 1/1992 |

| | | | | | |
|---|---|---|---|---|---|
| EP | 0513709 | 11/1992 | GB | 1577933 | 10/1980 |
| EP | 0542351 | 5/1993 | GB | 2264429 | 9/1993 |
| EP | 0558112 | 9/1993 | GB | 0028701.1 | 11/2000 |
| EP | 0258068 | 11/1993 | GB | 2358784 | 8/2001 |
| EP | 0238023 | 12/1993 | GB | 0301117.8 | 1/2003 |
| EP | 0575133 | 12/1993 | GB | 0301118.6 | 1/2003 |
| EP | 0580252 | 1/1994 | GB | 0301119.4 | 1/2003 |
| EP | 0258068 | 8/1994 | GB | 0301120.2 | 1/2003 |
| EP | 0622446 | 11/1994 | GB | 0301121.0 | 1/2003 |
| EP | 0 652 289 A1 | 5/1995 | GB | 0301122.8 | 1/2003 |
| EP | 0652289 | 5/1995 | GB | 2379165 | 3/2003 |
| EP | 0654527 | 5/1995 | GB | 2267033 | 11/2003 |
| EP | 0396162 | 9/1995 | GB | 0330016.7 | 12/2003 |
| EP | 0585988 | 3/1996 | JP | 59183881 | 4/1960 |
| EP | 0721981 | 7/1996 | JP | 48016612 | 12/1970 |
| EP | 0776604 | 6/1997 | JP | 55131340 | 10/1980 |
| EP | 0531104 | 8/1997 | JP | 60078529 | 5/1985 |
| EP | 0808903 | 11/1997 | JP | 62118883 | 11/1985 |
| EP | 0682116 | 12/1997 | JP | 63042691 | 8/1986 |
| EP | 0812910 | 12/1997 | JP | 62061590 | 3/1987 |
| EP | 0305216 | 3/1998 | JP | 62285749 | 12/1987 |
| EP | 0847701 | 6/1998 | JP | 10203974 | 8/1988 |
| EP | 0548228 | 8/1998 | JP | 1252294 | 10/1989 |
| EP | 0 882 797 A2 | 12/1998 | JP | 2-49593 | 2/1990 |
| EP | 0702712 | 12/1998 | JP | 2-153997 | 6/1990 |
| EP | 0882797 | 12/1998 | JP | 04075592 | 3/1992 |
| EP | 0897667 | 2/1999 | JP | 6014773 | 3/1992 |
| EP | 0913092 | 5/1999 | JP | 4121186 | 4/1992 |
| EP | 0913468 | 5/1999 | JP | 15626492 | 6/1992 |
| EP | 0321811 | 12/1999 | JP | 04200339 | 7/1992 |
| EP | 1131416 | 6/2000 | JP | 4300839 | 10/1992 |
| EP | 0739985 | 11/2000 | JP | 4327536 | 11/1992 |
| EP | 1057415 | 12/2000 | JP | 04-370055 | 12/1992 |
| EP | 1071734 | 1/2001 | JP | 5211852 | 8/1993 |
| EP | 0659049 | 3/2001 | JP | 05211852 | 8/1993 |
| EP | 1103606 | 5/2001 | JP | 6345800 | 12/1994 |
| EP | 1108360 | 6/2001 | JP | 07-079687 | 3/1995 |
| EP | 1138763 | 10/2001 | JP | 8268882 | 4/1995 |
| EP | 1145637 | 10/2001 | JP | 7231788 | 9/1995 |
| EP | 0191217 | 2/2002 | JP | 7330794 | 12/1995 |
| EP | 0869167 | 2/2002 | JP | 8143457 | 6/1996 |
| EP | 1193314 | 4/2002 | JP | 8266213 | 10/1996 |
| EP | 0746618 | 8/2002 | JP | 9040689 | 2/1997 |
| EP | 1233676 | 8/2002 | JP | 10155493 | 6/1998 |
| EP | 0648263 | 9/2002 | JP | 10155493 A | 6/1998 |
| EP | 0784674 | 9/2002 | JP | 11290078 | 10/1999 |
| EP | 1073339 | 11/2002 | JP | 2000226335 | 8/2000 |
| EP | 1275711 | 1/2003 | JP | 3553958 | 5/2004 |
| EP | 1285969 | 2/2003 | KR | 93-700773 | 3/1993 |
| EP | 1298205 | 4/2003 | KR | 94-10252 | 10/1994 |
| EP | 0635053 | 6/2003 | KR | 95-700043 | 1/1995 |
| EP | 0675944 | 6/2003 | KR | 95-702583 | 6/1995 |
| EP | 0817838 | 6/2003 | KR | 96-704602 | 8/1996 |
| EP | 1280919 | 6/2003 | KR | 2001-7012115 | 9/2001 |
| EP | 0746608 | 8/2003 | KR | 2003-7008997 | 10/2003 |
| EP | 0851913 | 5/2004 | NL | 0784674 | 12/2002 |
| EP | 1262562 | 6/2004 | NL | 0869167 | 1/2003 |
| EP | 1433852 | 6/2004 | NL | 1073339 | 2/2003 |
| EP | 0977869 | 7/2004 | NL | 0746608 | 11/2003 |
| EP | 0743017 | 9/2004 | RU | 2140751 | 6/1997 |
| EP | 0675949 | 10/2004 | RU | 2235775 | 11/1999 |
| EP | 0880590 | 10/2004 | RU | 2001117497 | 6/2001 |
| EP | 0897423 | 10/2004 | TR | 200101551 | 12/1999 |
| EP | 1466980 | 10/2004 | WO | 88/02775 | 4/1988 |
| EP | 0839186 | 11/2004 | WO | 88/03365 | 5/1988 |
| EP | 1162889 | 2/2005 | WO | WO 88/03365 | 5/1988 |
| EP | 1559788 | 8/2005 | WO | WO8901969 | 3/1989 |
| EP | 1363506 | 11/2005 | WO | 89/06803 | 7/1989 |
| ES | 535608 | 9/1984 | WO | 91/00920 | 1/1991 |
| ES | 535602 | 10/1984 | WO | WO 91/04669 | 4/1991 |
| ES | 535609 | 3/1985 | WO | 91/06661 | 5/1991 |
| GB | 1086550 | 10/1967 | WO | WO 91/06661 | 5/1991 |
| GB | 1442418 | 7/1976 | WO | 91/14772 | 10/1991 |

| | | |
|---|---|---|
| WO | 92/05249 | 4/1992 |
| WO | 92/14830 | 9/1992 |
| WO | WO 92/14830 | 9/1992 |
| WO | 92/18645 | 10/1992 |
| WO | 93/01285 | 1/1993 |
| WO | 93/11249 | 6/1993 |
| WO | 93/12812 | 7/1993 |
| WO | 94/01541 | 1/1994 |
| WO | 94/04035 * | 3/1994 |
| WO | WO 94/04035 | 3/1994 |
| WO | 94/14940 | 7/1994 |
| WO | 94/14951 | 7/1994 |
| WO | 94/26883 | 11/1994 |
| WO | 95/06720 | 3/1995 |
| WO | 95/09909 | 4/1995 |
| WO | 95/22606 | 8/1995 |
| WO | 95/22615 | 8/1995 |
| WO | 95/22625 | 8/1995 |
| WO | 95/29996 | 11/1995 |
| WO | 95/30744 | 11/1995 |
| WO | 96/09772 | 4/1996 |
| WO | 96/13578 | 5/1996 |
| WO | 96/13579 | 5/1996 |
| WO | 96/13580 | 5/1996 |
| WO | 96/27002 | 9/1996 |
| WO | 96/28542 | 9/1996 |
| WO | 96/30502 | 10/1996 |
| WO | 96/32472 | 10/1996 |
| WO | 96/39851 | 12/1996 |
| WO | 97/04079 | 2/1997 |
| WO | 97/05219 | 2/1997 |
| WO | 97/07202 | 2/1997 |
| WO | 97/07205 | 2/1997 |
| WO | 97/11083 | 3/1997 |
| WO | 97/14713 | 4/1997 |
| WO | WO 97/14713 | 4/1997 |
| WO | 97/27237 | 7/1997 |
| WO | 97/27276 | 7/1997 |
| WO | 97/41212 | 11/1997 |
| WO | 97/41735 | 11/1997 |
| WO | 97/41736 | 11/1997 |
| WO | WO 98/00029 | 1/1998 |
| WO | 98/08939 | 3/1998 |
| WO | 98/14594 | 4/1998 |
| WO | WO 98/16112 | 4/1998 |
| WO | 98/18912 | 5/1998 |
| WO | 98/26057 | 6/1998 |
| WO | WO 98/23162 | 6/1998 |
| WO | 98/31790 | 7/1998 |
| WO | 98/41623 | 9/1998 |
| WO | 98/44804 | 10/1998 |
| WO | 98/45453 | 10/1998 |
| WO | WO 98/45453 | 10/1998 |
| WO | 98/50532 | 11/1998 |
| WO | 98/51163 | 11/1998 |
| WO | 98/59028 | 12/1998 |
| WO | 99/33964 | 7/1999 |
| WO | 99/34011 | 7/1999 |
| WO | 99/37782 | 7/1999 |
| WO | 99/42566 | 8/1999 |
| WO | 99/50399 | 10/1999 |
| WO | 99/53001 | 10/1999 |
| WO | 99/53769 | 10/1999 |
| WO | 99/55883 | 11/1999 |
| WO | 00/05396 | 2/2000 |
| WO | WO 00/05396 | 2/2000 |
| WO | 00/28044 | 5/2000 |
| WO | 00/32758 | 6/2000 |
| WO | 00/34450 | 6/2000 |
| WO | 00/36114 | 6/2000 |
| WO | 00/43036 | 7/2000 |
| WO | 00/49164 | 8/2000 |
| WO | 00/58517 | 10/2000 |
| WO | 00/59307 | 10/2000 |
| WO | 00/60063 | 10/2000 |
| WO | 00/61771 | 10/2000 |
| WO | 00/71808 | 11/2000 |
| WO | 00/75295 | 12/2000 |
| WO | 01/16308 | 3/2001 |
| WO | 01/27251 | 4/2001 |
| WO | 01/29222 | 4/2001 |
| WO | 01/34835 | 5/2001 |
| WO | 01/39602 | 6/2001 |
| WO | 01/42433 | 6/2001 |
| WO | 01/47363 | 7/2001 |
| WO | 01/66711 | 9/2001 |
| WO | 01/78524 | 10/2001 |
| WO | 01/83559 | 11/2001 |
| WO | 01/83770 | 11/2001 |
| WO | 01/92502 | 12/2001 |
| WO | 02/00852 | 1/2002 |
| WO | 02/03805 | 1/2002 |
| WO | 02/06457 | 1/2002 |
| WO | 02/14490 | 2/2002 |
| WO | 02/24881 | 3/2002 |
| WO | 02/30207 | 4/2002 |
| WO | 02/055679 | 7/2002 |
| WO | 02/062973 | 8/2002 |
| WO | 02/065854 | 8/2002 |
| WO | 02/066622 | 8/2002 |
| WO | 02/094123 | 11/2002 |
| WO | 03/020923 | 3/2003 |
| WO | WO 03/020941 | 3/2003 |
| WO | 03/040091 | 5/2003 |
| WO | 03/060112 | 7/2003 |
| WO | 03/070013 | 8/2003 |
| WO | 03/089260 | 10/2003 |
| WO | 03/097825 | 11/2003 |
| WO | 03/099016 | 12/2003 |
| WO | 03/100044 | 12/2003 |
| WO | 03/102118 | 12/2003 |
| WO | 2004/004467 | 1/2004 |
| WO | 2004/018660 | 3/2004 |
| WO | 2004/053039 | 6/2004 |
| WO | 2004/053152 | 6/2004 |
| WO | 2004/059075 | 7/2004 |
| WO | 2004/064537 | 8/2004 |
| WO | 2004/064987 | 8/2004 |
| WO | 2004/097012 | 11/2004 |
| WO | 2004/111216 | 12/2004 |
| WO | 2005/003339 | 1/2005 |
| WO | 2005/005977 | 1/2005 |
| WO | 2005/056782 | 6/2005 |
| WO | 2005/066347 | 7/2005 |
| WO | 2005/066351 | 7/2005 |
| WO | 2005/080540 | 9/2005 |
| WO | 2005/087918 | 9/2005 |
| WO | 2006/008508 | 1/2006 |
| WO | 2006/008653 | 1/2006 |
| WO | 2006/032279 | 3/2006 |
| WO | WO 2008/094847 | 8/2008 |

OTHER PUBLICATIONS

Blecker, C. et al., "Improved Emulsifying and Foaming of Why Proteins after Enzymic Fat Hydrolysis." Journal of Food Service, 1997, 62(1):48-52.

Coteron, A. et al., "Reactions of Olive Oil and Glycerol over Immobilized Lipases," *JAOCS*, 75(5):657-660, 1998.

McNeill, G. et al., "High-Yield Enzymatic Glycerolysis of Fats and Oils," *JAOCS*, 68(1): 1-5, 1991.

Spradlin, J., "Tailoring Enzyme Systems for Food Processing," In *Biocatalysis in Agricultural Biotechnology*, Eds.: Whitaker J. and Sonnet, P., ACS Symposium Series 389, American Chemical Society, Washington, DC, 1989, pp. 24-43.

Yamane, T. et al., "High-Yield Diacylglycerol Formation by Solid-Phase Enzymatic Glycerolysis of Hydrogenated Beef Tallow," JAOCS, 71(3): 339-42, 1994.

U.S. Appl. No. 60/039,791, filed Mar. 4, 1997, Clausen.

U.S. Appl. No. 60/189,780, filed Mar. 16, 2000, Soe.

U.S. Appl. No. 60/489,441, filed Jul. 23, 2003, Kreij.

U.S. Appl. No. 60/039,791, filed Mar. 4, 1997, Clausen.

Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.

Kuwabara, et al., "Purification and Some Properties of Water-soluble Phospholipase B from *Torulaspora delbrueckii*", J. Biochem., vol. 104, pp. 236-241, 1988.

Kuwabara, et al., "Purification and Some Properties of Water-soluble Phospholipase", Agric. Biol. Chem., vol. 52, No. 10, pp. 2451-2458, 1988.

Kweon et al., "Phospholipid Hydolysate and Antistaling Amylase Effects on Retrogradation of Starch in Bread", Journal of Food Science, vol. 59, No. 5, 1994.

Larsen N G et al, Journal of Cereal Science (1990), vol. 12(2), pp. 155-164.

Lee, Keun Hyeung, et al., "Identification and characterization of the antimicrobial peptide corresponding to C-terminal B-sheet domain of tenecin 1, an antibacterial protein of larvae of Tenebrio molitor", Biochem. J., 1996, vol. 334, pp. 99-105.

Leggio, Leila Lo, et al., "The 1.62 A structure of Thermoascus aurantiacus endoglucanase: completing the structural picture of sub-families in glycoside hydrolase family 5", FEBS Letters, vol. 523, 2002, pp. 103-108.

Leidich et al., "Cloning and Disruption of caPLB1, a Phospholipase B Gene Involved in the Pathogenicity of Candida albicans", The Journal of Biological Chemistry, vol. 273, No. 40, oo. 26078-26086, 1998.

Li, W., et al., "Surface properties and locations of gluten proteins and lipids revealed using confocal scanning laser microscopy in bread dough", Journal of Cereal Science, vol. 39, 2004, pp. 403-411.

Lih-ling Wang et al, J Agric. Food. Chem. (1993), 41, 1000-1005.

Lima, Vera L.M., et al., "Lecithin-cholesterol acyltransferase (LCAT) as a plasma glycoprotein: an overview", Carbohydrate Polymers, vol. 55, 2004, pp. 179-191.

Lin M J Y et al, Cereal Chemistry (1974), vol. 51(1), p34-45.

Lin S et al, Enzyme and Microbial Technology 18 (1996), pp. 383-387.

Lipase A "Amano" 6 Assay Note and Product Specification from Armano Pharmaceutical Co Ltd Nagoya Japan, Dec. 16, 1985.

Lipase A "Amano" 6 Assay Note and Product Specification from Armano Pharmaceutical Co Ltd Nagoya Japan, Aug. 27, 1985.

Lipase A "Amano" 6 product sheet, Apr. 1, 1999.

Lipase SP677 as a Baking Enzyme, from Novo Nordisk, Denmark, Mar. 17, 1994.

Lipopan F: Keep the quality—cut your costs 2000 Novozymes A/S. www.enzymes.novo.dk/cgl-bin/bvisapi.dll/biotimes/one_article.jsp?id=16947&lang=en&t=b1.

Litthauer, Derek, et al., "Pseudomonas luteola lipase: A new member of the 320- residue Pseudomonas lipase family", Enzyme and Microbial Technology, vol. 30, pp. 209-215, 2002.

Llustenberger, Cornelia, et al., "Application of Noopazyme in Asian Noodles and Non-Durum Pasta", Cereal Food, 2002-18584-01, p. 1, vol. 11.

Llustenberger, Cornelia, et al., "Enzymes in Frozen Dough and Parbaked Bread", Cereal Food, 2001-17056-01, p. 1, vol. 19.

Longhi, Sonia, et al., "Atomic Resolution (1.0 Å) Crystal Structure of Fusarium solani Cutinase: Stereochemical Analysis" J. Mol. Biol. vol. 268, pp. 779-799, 1997.

Lozano et al., "Over-stabilization of *Candida antarctica* lipase B by ionic liquids in ester synthesis", Biotechnology Letters, vol. 23, pp. 1529-1533, 2001.

Luzi, Paola et al, Genomics (1995), vol. 26(2), p407-9.

Madsen J.S. & Qvist K.B. (1997) J. Food Sci. 62, 579-582.

Mao, Cungui, et al., "Cloning and Characterization of a *Saccharomyces cerevisiae* Alkaline Ceramidase with Specificity for Dihydroceramide", The Journal of Biological Chemistry, vol. 275, No. 40, 2000, pp. 31369-31378.

Maria Teres Neves Petersen, PhD, "Total Internal Reflection Fluorescence Flow System with Electrochemical Control", TIRF-EC Flow System, Sep. 2002.

Marion D et al—Chapter 6, pp. 131-p. 167 of "Interactions The Keys to Cereal Quality" 1998 ISBN 0 913250-99-6 (ed. Hamer & Hoseney).

Marsh, Derek, et al., "Derivastised lipids in membranes. Physico-chemical aspexts of N-biotinyl phosphatidylethanolamines and N-acyl ethanolamines", Chemistry and Physics of Lipids, vol. 105, 2000, pp. 43-69.

Martinelle et al., "The Role of Glu87 and Trp89 in the lid of *Humicola lanuginosa* lipase", Protein Engineering, vol. 9, No. 6, 1996, pp. 519-524.

Martinez, Chrislaine, et al., "Engineering cysteine mutants to obtain crystallographic phases with a cutinase from Fusarium solani pisi", Protein Engineering, vol. 6, No. 2, pp. 157-165, 1993.

Martinez, Diego, et al., "Genome sequence of the lignocellulose degrading fungus *Phanerochaete chrysosporium* strain RP78", Nature Biology, May 2, 2004.

Mase et al., "Purification and Characterization of a new Lipase from Fusarium sp. TM-30", Biosci. Biotech. Biochem., vol. 59, No. 9, pp. 1771-1772, 1995.

Mason, Research Disclosure, Kenneth Mason Publications, Westbourne GB No. 390, Oct. 1996, pp. 661-662.

Masuda, Naoka, et al., "Primary structure of protein moiety of *Penicillium notatum* phospholipase B deduced from the Cdna", Eur. J. Biochem., vol. 202, pp. 783-787, 1991.

Matos AR, Lipid Catabolism: Lipid Degradation, 2000, pp. 779-781.

Matos, A.R., et al., "A patatin-like protein with galactolipase activity is induced by drought stress in *Vigna unguiculata* leaves", Biochemical Society Transactions, vol. 28, part 6, 2000.

Matos, AR et al, Febs Letters, 491 (2001) pp. 188-192.

Matsuda H et al, Biochim Biophys Acta, (1979), vol. 573(1), p155-65.

Matsuoka, et al.; "Purification and properties of a Phospholipase C That has High Activity toward Sphingomyelin from *Aspergillus saitoi*"; Biotiechonology and Applied Biochemistry (1987); vol. 9, pp. 401-409.

Matthes et al, (1984) EMBO J. 3, p801-805.

McAuley, Katherine E., et al., "Structure of a feruloyl esterase from *Aspergillus niger*", Acta Crystallographica, Section D, pp. 878-887; 2004.

McCoy M G et al, Journal of Lipid Research (2002), vol. 43, pp. 921-929.

McNeill G.P. & Berger R.G. (1993) Enzymatic glycerolysis of palm oil fractions and palm oil based model mixture: Relationship between fatty acid composition and monoglyceride yield, in Food Biotechnology 7: 75-87.

McNeill, Gerald P., et al., "High-Yield Enzymatic Glycerolysis of Fats and Oils", JAOCS, vol. 68, No. 1, Jan. 1991.

McNeill, Gerald P., et al., "Selective Distribution of Saturated Fatty Acids into the Monoglyceride Fraction During Enzymatic Glycerolysis", JAOCS, vol. 69, No. 11, Nov. 1992.

Memo: From Charlotte Johanson?, "Short introduction/ status on Ferulic Acid Esterases and Acetyl Xylan Esterases", Jan. 9, 2004.

Meyer, V., et al., "Transcriptional regulation of the Antifungal Protein in *Aspergillus giganteus*", Mol Genet Genomics, 2002, vol. 266, pp. 747-757.

Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.

Mielgo, I., et al., "Covalent immobilisation of manganese peroxidases (MnP) from *Phanerochaete chrysosporium* and Bjerkandera sp. BOS55", Enzyme and Microbial Technology, vol. 32, 2003, pp. 769-775.

Miller, Byron S., et al., "A Comparison of Cereal, Fungal, and Bacterial Alpha-Amylases as Supplements for Breadmaking", Food Technology, Jan. 1953.

Mine Y, Food Research International, 29(1), 1996, pp. 81-84.

Ministerio da Ciencia e Tecnologia, *Diario Oficial da Uniao*, Jul. 15, 2003.

Mogensen, Jesper E., et al., "Activation, Inhibition, and Destabilization of Thermomyces lanuginosus Lipase by Detergents", Biochemistry, vol. 44, pp. 1719-1730, 2005.

Molecular Biological Methods for Bacillus—Chapter 3 (Ed. C.R. Harwood and S.M. Cutting) 1990, John Wiley and Sons Ltd, Chichester, UK.

Mølgaard, Anne, et al., "Rhamnogalacturonan acetylesterase elucidates the structure and function of a new family of hydrolases", Structure, vol. 9, No. 4, 2000.

Molochnaya Promyshlennost 1980 No. 11 21-25, 47—abstract from Food Sci & Tech Abs.

Monographs for Emulsifiers for Foods, EFEMA Nov. 1985 2nd Edition.

Moore, Charles M., et al., "Metal ion homeostasis in *Bacillus subtilis*", Current Opinion in Microbiology, 2005, vol. 8, pp. 188-195.

Morgan, Keith R., et al., "Stalling in Starch Breads: The Effect of Antistaling α-Amylase", Starch/Stärke, vol. 49, 1997, pp. 59-66.

Morgan-Jones, Gareth; "Notes on Coelomycetes.II. Concerning the Fusicoccum Anamorph of Botryosphaneria Ribis"; vol. Xxx, pp. 117-125; Oct.-Dec. 1987.

Morinaga et al Biotechnology (1984) 2, p636-639.

Morten, T. & A., Letter, Rodovre, Jul. 2004.

Mukherjee, Kumar D. et al., "Enrichment of y-linolenic acid from fungal oil by lipase-catalysed reactions", Appl. Microbiol Biotechnol (1991), vol. 35, pp. 579-584.

Murakami, Nobutoshi, et al., "Enzymatic Transformation of Glyceroglycolipids into sn-1 and sn-2 Lysoglyceroglycolipids by use of *Rhizopus arrhizus* Lipase", Tetrahedron, vol. 50, No. 7, pp. 1993-2002, 1994.

Mustranta, Annikka, et al., "Comparison of Lipases and Phosphlipases in the Hydrolysis of Phospholipids", Process Biochemistry, vol. 30, No. 5, pp. 393-401, 1995.

Nagano, et al.; "Cloning and Nucleotide Sequence of cDNA Encoding a Lipase from *Fusarium keteroporum*"; J. Biochem (1994); vol. 116; pp. 535-540.

Nagao et al, J. Biochem 124, 1124-1129, 1998.

Nagao et al, J. of Bioscience and Bioengineering vol. 89, No. 5, 446-450, 2000.

Nagao et al, J. of Molecular Catalysis B: Enzymatic 17 (2002) 125-132.

Nagao et al, JAOCS vol. 78, No. 2, 2001.

Nagao, Toshihiro et al., "Cloning and Nucleotide Sequence of CDNA Encoding a Lipase from Fusarium heterosporum", J. Biochem., vol. 116, pp. 535-540, 1994.

Nagao, Toshihiro et al., "Expression of Lipase of cDNA from Fusarium heterosporum by *Saccharomyces cereviisiae*: High-Level Production and Purification", Journal of Fermentation and Bioengineering, 1996, vol. 81, No. 6, pp. 488-492.

Nagodawlthana et al., "Enzymes in Food Processing", Third Edition, 1993, Academic Press, Inc.

National Research Council (U.S.) Committee on Specifications of the Food Chemicals Codex, "Lipase Activity" in *Food Chemicals Codex* (1981) National Academy Press, Washington, D.C. pp. 492-493.

Needleman & Wunsch (1970), J. of Molecular Biology 48, 443-453.

Nelson and Long, Analytical Biochemistry (1989), 180, p. 147-151.

Nerland A H, Journal of Fish Diseases, vol. 19, No. 2, pp. 145-150.

Ness, Jon. E., et al., "DNA shuffling of subgenomic sequences of subtilisin" Nature Biotechnology, vol. 17, Sep. 1999.

Nestle Research Center, Brochure for "Food Colloids 2006" in Montreux, Switzerland, Apr. 23-26, 2006.

Neugnot Virginie et al, European Journal of Biochemistry, 2002, vol. 269, pp. 1734-1745.

Newport, G., et al., "KEX2 Influences *Candida albicans* Proteinase Secretion and Hyphal Formation", The Journal of Biological Chemistry, 1997, vol. 272, No. 46, pp. 28954-28961.

Nicolas, Anne, et al., "Contribution of Cutinase Serine 42 Side Chain to the Stabilization of the Oxyanion Transition State", Biochemistry, vol. 35, pp. 398-410, 1996.

Nierle W et al, Fette Seifen Anstrichmittel (1981), vol. 83(10), p391-395.

Nierle, W., et al., "Versuche zur Verlangerung der Haltbarkeit von Dartoffelprodukten", Chem. Mikrobiol. Technol. Lebensm., 1975, vol. 3, pp. 172-175.

Nobutoshi M et al, Tetrahedron Letters (1991), vol. 31(1), p1331-4.

Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".

Novozymes Memo—Test of lipases for EP1193314B1, Jul. 6, 2005.

Novozymes Report 2002 Annual Report.

Novozymes, "Biowhitening—a new concept for steamed bread", *BioTimes*, Jan. 2005.

Novozymes, "Breakthrough: Less Fattening Fried Food" *BioTimes*, Jun. 2001, No. 2.

Novozymes, "Enzymes for dough strengthening", 2001.

Novozymes, "Lipopan F BG- application and mechanism of a new lipase for bread baking" (Draft) *Cereal Food* (2003) (Author: Drost-Lustenberger, C. et al.).

Novozymes, "Product Sheet for Lipopan F BG", *Cereal Food*, (2001).

Novozymes, "Product Sheet for Lipopan FS BG", *Cereal Food* (2002).

Novozymes, "Product Sheet for Lipopan S BG", *Cereal Food* (2002).

Novozymes, "Revolutionizing baking", *BioTimes* (2002) pp. 6-7.

Novozymes, "Strong sales for lipase that makes dough stronger" *BioTimes*, Dec. 2003.

Novozymes, "The perfect roll every time for steers", *BioTimes*, Sep. 2003.

Novozymes, "The value of innovation", *BioTimes*, Mar. 2004.

Novozymes, "The vital role of technical service in baking", *BioTimes*, Jun. 2004.

Ohm, J.B., et al., "Relationships of Free Lipids with Quality Factors in Hard Winter Wheat Flours", Cereal Chem., vol. 79, No. 2, pp. 274-278, 2002.

Ohta, S. et al., "Application of Enzymatic Modification of Phospholipids on Breadmaking", Abstract from AACC 68th Annual Meeting in Kansas City, MO, Oct. 30th-Nov. 3, 1983, published in Cerial Foods World, p. 561.

Ohta, Yoshifumi, et al., "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.

Okiy D.A. (1977) Partial glycerides and palm oil Crystallisation, in Journal of Science and Food Agriculture 28:955.

Okiy D.A. (1978) Interaction of triglycerides and diglycerids of palm oil, in Oleagineux 33:625-628.

Okiy D.A., Wright, W.B., Berger, K.G. & Morton I.D. (1978), The physical properties of modified palm oil, in Journal of Science of Food and Agriculture 29:1061-1068.

Oluwatosin, Yemisi E., et al., "Phenotype: a Possible Role for the Kex2 Endoprotease in Vacuolar Acidification", Molecular and Cellular Biology, 1998, pp. 1534-1543.

Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.

Orberg, Marie-Louise, "Self-assembly Structures Formed by Wheat Polar Lipids and their Interaction with Lipases", Master of Scient Thesis, Apr. 2005.

Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.

Osman, Mohamed, et al., "Lipolytic activity of Alternaria alternata and Fusarium oxysporum and certain properties of their lipids", Microbios Letters, vol. 39, pp. 131-135, 1988.

O'Sullivan et al, J Plant Physiol, vol. 313, (1987) p393-404.

Palomo, Jose M., et al., "Enzymatic production of (3S, 4R)-(-)-4-(4'-fluorophenyl)-6-oxo-piperidin-3-carboxylic acid using a commerical preparation of lipase A from *Candida antarctica*: the role of a contaminant esterase" Tetrahedron: Asymmetry, vol. 13, 2002, pp. 2653-2659.

Palomo, Jose M., et al., "Enzymatic resolution of (±)-glycidyl butyrate in aquenous media. Strong modulation of the properties of the lipase from *Rhizopus oryzae* via immobilization techniques", Tetrahedron: Asymmetry, vol. 15, 2004, pp. 1157-1161.
Palomo, Jose M., et al., "Modulation of the enantioselectivity of *Candida antarctica* B lipase via conformational engineering: kinetic resolution of (±)-α-hydroxy-phenylacetic acid derivatives", Tetrahedron: Asymmetry, vol. 13, 2002, pp. 1337-1345.
Patent Abstracts of Japan vol. 016, No. 528 (C-1001), Oct. 29, 1992 & JP 04 200339 A see abstract.
Patent Abstracts of Japan vol. 095, No. 001, Feb. 28, 1995 & JP 06 296467 A see abstract.
Peelman F, et al, Protein Science Mar. 1998; 7(3): 587-99.
Penninga et al, Biochemistry (1995), 3368-3376.
Persson, Mattias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the *Humicola lanuginosa* Lipase", Biochemistry, 1998, vol. 37, pp. 12375-12383.
Peters, Günther H., et al., "Theoretical Investigation of the Dynamics of the Active Site Lid in *Rhizomucor miehei* Lipase", Biophysical Journal, vol. 71, 1996, pp. 119-129.
Plijter J and JHGM Mutsaers, The surface rheological properties of dough and the influence of lipase on it, Gist-brocades, Bakery Ingredients Division, Oct. 1994.
Plou et al, J. Biotechnology 92 (2002) 55-66.
Ponte J G, Cereal Chemistry (1969), vol. 46(3), p325-29.
Punt and van den Hondel, Meth. Enzym., 1992, 216:447-457.
Pyler, E.J., "Baking Science and Technology Third Edition", vol. 1, 1988.
Pyler, E.J., "Baking Science and Technology Third Edition", vol. II, 1988.
Queener et al. (1994) Ann N Y Acad Sci. 721, 178-93.
Rambosek and Leach, CRC Crit. Rev. Biotechnol., 1987, 6:357-393.
Rapp, Peter, et al., "Formation of extracellular lipases by filamentous fungi, yeasts, and bacteria", Enzyme Microb. Technol., 1992, vol. 14, November.
Rapp, Peter; "Production, regulation, and some properties of lipase activity from *Fusarium oxysporum* f. sp. *vasinfectum*"; Enzyme and Microbial Technology(1995); vol. 17; pp. 832-838.
Reetz M.T., Jaeger K.E. Chem Phys Lipids. Jun. 1998; 93(1-2): 3-14.
Reetz Manfred T, Current Opinion in Chemical Biology, Apr. 2002, vol. 6, No. 2, pp. 145-150.
Reiser J et al. (1990) Adv Biochem Eng Biotechnol. 43, 75-102.
Richardson & Hyslop, pp. 371-476 in Food Chemistry, 1985, second edition, Owen R. Fennema (ed), Manel Dekker, Inc, New York and Basel.
Richardson and Hyslop, "Enzymes: XI—Enzymes Added To Foods During Processing" in *Food Chemistry*, Marcel Dekker, Inc., New York, NY 1985.
Arskog and Joergensen, "Baking performance of prior art lipases from *Candida cylindracea* and *Aspergillus foeditus* and their activity on galactolipids in dough", Novozymes Report 2005.
Arskog and Joergensen, "Baking performance of prior art lipases from *Humicola lanuginosa, Aspergillus tubigensis, Rhizopus delemar* and *Rhizomucor miehei*, and their actiivty on galactolipids in dough", Novozymes Report 2005.
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) Gene 122(1), 155-61.
Roberts, et al.; "Extracellular Lipase Production by Fungi from Sunflower Seed", Mycologia(1987); vol. 79(2); pp. 265-273.
Robertson et al, Journal of Biological Chemistry, 1994, 2146-2150.
Rodrigues, et al.;"Short Communication: Bioseparations with Permeable Particles", Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.

Rousseau, Derick, et al., "Tailoring the Textural Attributes of Butter Fat/Canola Oil Blends via *Rhizopus arrhizus* Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in *Vigna unguiculata* leaves and influence of drought stress", Physiologia Plantarum, vol. 104, pp. 577-586, 1998.
Sahsah, Y., et al., "Purification and characterization of a soluble lipolytic acylhydrolase from Cowpea (*Vigna unguiculata* L.) leaves", Biochimica et Biophysica Acta, vol. 1215, pp. 66-73, 1994.
Saiki R.K. et al Science (1988) 239, pp. 487-491.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p291-294, Publisher Kluwer Academic Publishers.
Sambrook et al, Chapters 1, 7, 9, 11, 12 and 13—Molecular Cloning a laboratory manual, Cold Spring Harbor Laboratory Press (1989).
Sambrook, J., et al. "A Laboratory Manual, Second Edition", Plasmid Vectors, 1989.
Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.
Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).
Saxena, et al.; "Purification Strategies for Microbial Lipases"; Journal of Microbilogical Methods (2003); pp. 1-18.
Scheib et al.; "Stereoselectivity of Mucorales lipases toward triradylglycerols—A simple solution to a complex problem"; Protein Science (1999); vol. 8; pp. 215-221.
Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.
Scopes, Robert K., "Section 8.4: Ultrafiltration" in *Protein Purification Principles and Practice, Third Edition* (1994) Springer-Verlag, New York, p. 267-9.
Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.
Shimada et al, J. of Bioscience and Bioengineering vol. 91, No. 6, 529-538 (2001).
Shimada et al, J. of Fermentation and Bioengineering vol. 75, No. 5, 349-352 (1993).
Shimada et al, JAOCS vol. 71, No. 9, (Sep. 1994).
Shin, et al.; "Butyl-Toyopearl 650 as a New Hydrophobic Adsorbent for Water-Soluable Enzyme Proteins"; Analytical Biochemistry(1984); vol. 138; pp. 259-261.
Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969.
Si, Joan Qi; "New Enzymes for the Baking Industry"; Food Tech Europe (1996) pp. 60-64.
Sias B et al, Biochemistry, (2004), vol. 43(31), p10138-48.
Siew W.L. & Ng W.L. (1999) Influence of diglycerides on crystalisation of palm oil, in Journal of Science of Food and Agriculture 79:722-726.
Siew W.L. & Ng W.L. (2000) Differential scanning thermograms of palm oil triglycerides in the presence of diglycerides, in Journal of Oil Palm Research 12:107.
Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.

Skovgaard, et al.;"Comparison of Intra- and extracellualr isozyme banding patterns of *Fusarium oxysporum*"; Mycol. Res. (1998); vol. 102(9); pp. 1077-1084.
Slotboom et al Chem. Phys. Lipids 4 (1970) 15-29.
Smith, George P.; "The Progeny of sexual PCR"; Nature; vol. 370; No. 18; Aug. 4, 1994.
Smith, Timothy L., et al., "The promoter of the glucoamylase-encoding gene of *Aspergillus niger* functions in *Ustilago maydis*", Gene. 88, 259-262, 1990.
Solares, Laura F., et al., "Enzymatic resolution of new carbonate intermediates for the synthesis of (S)-(+)-zopiclone", Tetrahedron: Asymmetry, vol. 13, 2002, pp. 2577-2582.
Sols and De Le Fuente, "On the substrate specificity of glucose oxidase", Biochem et Biophysica Acta (1957) 24:206-7.
Sonntag N.O.V. (1982a) Glycerolysis of Fats and methyl esters—status, review and critique, in Journal of American Oil Chemist Society 59:795-802A.
Soragni, Elisabetta, et al., "A nutrient-regulated, dual localization phospholipase A2 in the symbiotic fungus" The EMBO Journal, vol. 20, No. 18, pp. 5079-5090, 2001.
Sosland, Josh, "Alive and kicking", Milling & Baking News, Feb. 24, 2004.
Soumanou, Mohamed M., et al., "Two-Step Enzymatic Reaction for the Synthesis of Pure Structured Triacylglycerides", JAOCS, vol. 75, No. 6, 1998.
Spendler, et al., "Functionality and mechanism of a new 2nd generation lipase for baking industry"—Abstract. 2001 AACC Annual Meeting; Symposia at Charlotte, NC. Oct. 14-18, 2001.
Spradlin J E, Biocatalysis in Agric. Technol., ACS Symposium, 389(3), 24-43 (1989).
Sreekrishna K et al (1988) J Basic Microbiol. 28(4), 265-78.
Stadler et al., "Understanding Lipase Action and Selectivity", CCACAA, vol. 68, No. 3, pp. 649-674, 1995.
Steinstraesser, et al., "Activity of Novispirin G10 against Pseudomonas aeruginosa In Vitro and in Infected Burns", Antimicrobial Agents and Chemotherapy, Jun. 2002, vol. 46, No. 6, pp. 1837-1844.
Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.
Stemmer, Willem P.C.; "Rapid evolution of a protein in vitro by DNA shuffling"; Affymax Research Institute, Nature, vol. 370, Aug. 4, 1994.
Sternberg, M., "Purification of Industrial Enzymes with Polyacrylic Acids", Process Biochemistry, Sep. 1976.
Strickland, James A., et al., "Inhibition of Diabrotica Larval Growth by Patatin, the Lipid Acyl Hydrolase from Potato Tubers", Plant Physiol, vol. 109, pp. 667-674, 1995.
Sudbery et al (1988) Biochem Soc Trans. 16(6), 1081-3.
Sugatani, Junko, et al., "Studies of a Phospholipase B from Penicillium Notatum Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Sugiyama et al., "Molecular cloning of a second phospholipase B gene, caPLB2 from *Candida albicans*", Medical Mycology, vol. 37, 1999.
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the Pseudomonas family", Biochimica et Biophysica Acta, vol. 1259, 1995, pp. 9-17.
Sweigard, James A., et al., "Cloning and analysis of CUT1, a cutinase gene from *Magnaporthe grisea*", Mol. Gen. Genet., 232:174-182, 1992.
Swinkels et al (1993) Antonie van Leeuwenhoek 64, 187-201.
Sztajer H et al Acta Biotechnol, vol. 8, 1988, pp. 169-175.
Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.

Terasaki, Masaru, et al., "Glycerolipid Acyl Hydrolase Activity in the Brown Alga *Cladosiphon okamuranus* Tokida", Biosci. Biotechnol. Biochem., vol. 67, No. 9, pp. 1986-1989, 2003.
The New Enzyme Operatives, Ingredient Technology, 50, Aug. 1997.
Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et al 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.
Toida J et al, Bioscience, Biotechnology, and Biochemistry, Jul. 1995, vol. 59, No. 7, pp. 1199-1203.
Tombs and Blake, Biochim. Biophys (1982) 700:81-89.
Topakas, E., et al. "Purification and characterization of a feruloyl esterase from *Fusarium oxysporum* catalyzing esterification of phenolic acids in ternary water—organic solvent mixtures", Journal of Biotechnology, vol. 102, 2003, pp. 33-44.
Torossian and Bell (Biotechnol. Appl. Biochem., 1991, 13:205-211.
Tsao et al. (1973) J Supramol Struct. 1(6), 490-7.
Tsuneo Yamane et al., "Glycerolysis of Fat by Lipase", Laboratory of Bioreaction Engineering, vol. 35, No. 8, 1986.
Tsychiya, Atsushi, et al., "Cloning and nucleotide sequence of the mono- and diacylglycerol lipase gene (mdlB) of *Aspergillus oryzae*", FEMS Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.
Turner, Progress in Industrial Microbiology, Martinelli and Kinghorn (eds.), Elsevier, Amsterdam, 1994, 29:641-666.
Unknown, *Studies on Lipase* (1964) p. 21.
Uppenberg, Jonas, et al., "Crystallographic and Molecular-Modeling Studies of Lipase B from *Candida antarctia* Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from *Candida antarctica*", Structure 1994, vol. 2, No. 4.
Upton C et al TIBS Trends in Biochemical Sciences, Elsevier Publication (1995), vol. 20, pp. 178-179.
Uusitalo et al. (1991) J Biotechnol. 17(1), 35-49.
Uwajima T et al, Agricultural and Biological Chemistry, 43(12), pp. 2633-2634, 1979.
Uwajima T et al, Agricultural and Biological Chemistry, 44(9), pp. 2039-2045, 1980.
Vaidehi, et al.; "Lipase Activity of Some Fungi Isolated from Groundnut"; Current Science (1984); vol. 53(23); p. 1253.
van Binsbergen, Jan, et al., "Substitution of Phe-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.
van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.
van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.
van Oort, Maarten G et al, Biochemistry 1989 9278-9285.
Vaysse et al J. of Biotechnology 53 (1997) 41-46.
Villenueva, Inform, vol. 8, No. 6, Jun. 1997.
Vujaklija, Dušica, et al., "A novel Streptomycete lipase: cloning, sequencing and high-level expression of the *Streptomyces rimosus* GDS (L)-lipase gene", Arch. Microbiol. vol. 178, pp. 124-130, 2002.
Wahnelt S.V., Meusel D, & Tülsner M, (1991) Zur kenntnis des diglyceride influsses auf das kristallisationsverhalten von Fetten, in Fat Science Technology 4:117-121.
Waninge, Rianne, et al., "Milk membrane lipid vesicle structures studied with Cryo-TEM", Colloids and Surfaces B: Biointerfaces 31 (2003), pp. 257-264.
Warmuth et al, 1992, Bio Forum 9, 282-283.
Watanabe et al. Bio sci Biochem 63(5) 820-826, 1999.

Watanabe, Yasuo et al., "Cloning and sequencing of phospholipase B gene from the yeast *Torulaspora delbrueckii*", FEMS Microbiology Letters, vol. 124, 1994, pp. 29-34.

Webb EC, Enzyme Nomenclature, 1992, p. 310.

Weber et al. J Agric Food Chem 1985, 33, 1093-1096.

Wen-Chen Suen et al., "Improved activity and thermostability of *Candida antarctica* lipase B by DNA family shuffling", Protein Engineering, Design & Selection, vol. 17, No. 2, pp. 133-140, 2004.

West S.; "Olive and Other Edible Oils"; Industrial Enzymology (1996); pp. 295-299.

Whitehead, Michael, et al., "Transformation of a nitrate reductase deficient mutant of *Penicillium chrysogenum* with the corresponding *Aspergillus niger* and A. nidulans niaD genes", Mol Gen Genet, 216: 408-411, 1989.

Wilhelm et al., "A Novel Lipolytic Enzyme Located in the Outer Membrane of *Pseudomonas aeruginosa*", Journal of Bacteriology, vol. 181, No. 22, Nov. 1999, pp. 6977-6986.

Winnacker, Chapter 11, pp. 424-431 In From genes to clones: introduction to gene technology, VCH (1987).

Winnacker, E. "Chapter 11: Identification of Recombinant DNA" in *From Genes to Clones: Introduction to Gene Technology*, 1987 John Wiley & Sons.

Winther, Ole, et al., "Teaching computers to fold proteins", Physical Review, vol. 70, No. 030903, 2004.

Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.

Witt, Wolfgang et al., "Secretion of Phospholipase B From *Saccharomyces cerevisiae*", Biochimica et Biophysica Acta, vol. 795, 1984, pp. 117-124.

Wood et al., Eds., "Biomass, Part B, Lignin, Pectin, and Chitin", Methods in Enzymology (1988) vol. 161, Academic Press, San Diego.

Xu, Jun, et al., "Intron requirement for AFP gene expression in *Trichoderma viride*", Microbiology, 2003, vol. 149, pp. 3093-3097.

Yamaguchi et al, 1991, Gene 103:61-67.

Yamane et al., "High-Yield Diacylglycerol Formation by Solid-Phase Enzymatic Glycerolysis of Hydrogenated Beef Tallow", JAOCS, vol. 71, No. 3, Mar. 1994.

Yamauchi, Asao et al., "Evolvability of random polypetides through functional selection within a small library", Protein Engineering, vol. 15, No. 7, pp. 619-626, 2002.

Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.

Zaks, Aleksey, et al., "Enzyme-catalyzed processes in organic solvents", Proc. Natl. Acad. Sci. USA, vol. 82, pp. 3192-3196, May 1985.

Zaks, Aleksey, et al., "The Effects of Water on Enzyme Action in Organic Media", The Journal of Biological Chemistry, vol. 263, No. 17, Issue of Jun. 15, pp. 8017-8021, 1988.

Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.

Zangenbert, Niels Honberg, et al., "A dynamic in vitro lipolysis model II. Evaluation of the model", European Journal of Pharmaceutical Sciences, vol. 14, 2001, pp. 237-244.

Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.

Acker, L. "Die Lipide des Getreides, ihre Zusammense und inre Bedeutung", Getreide Mehl Brot (1974) 28:181-187.

Adamzcak, Marek, et al., "Application of Enzymatic Glycerolysis for Production of Monoglycerides from Waste Fats", Polish Journal of Food and Nutrition Science, Mar. 1994.

Adhikari, B., et al., "Stickiness in Foods: A Review of Mechanisms and Test Methods", International Journal of Food Properties, vol. 4, No. 1, 2001.

Agarwal et al., "Lipase Activity of Some Fungi Isolated from Groundnut", Current Science, Dec. 5, 1984, vol. 53, No. 23.

Aires-Barros et al (1994) Isolation and purification of lipases, Cambridge Unversity Press.

Aisaka, Kazuo et al., "Production of Lipoprotein Lipase and Lipase by *Rhizopus japonicu*", Agri. Biol. Chem., vol. 43, No. 10, pp. 2125-2129, 1979.

Akoh, Casimir C., et al., "GDSL family of serine esterases/lipases" Progress in Lipid Research, vol. 43, 2004, pp. 534-552.

Allan Svendsen et al., "Biochemical properties of cloned lipases from the Pseudomonas family", Biochimica et Biophysica Acta, vol. 1259, 1995, pp. 9-17.

Al-Obaidy, K A, Dissertation Abstracts International B (1987) vol. 47(9) 3597, order No. DA8624641, pp. 266.

Amano Enzyme Inc. (2004). Http://www.amano-enzyme.co.jp/english/productuse/oil_fat.html. Dato 21.06.04.

Amano Enzymes "Enzymes for Gastrointestinal Digestion" Oct. 1997.

Amano Enzymes, Amano Enzyme Europe Ltd, Sep. 1994.

Amin, Neelam S., et al., "Direct transformation of site-saturation libraries in *Bacillus subtilis*", BioTechniques, Dec. 2003, 35:1134-1140.

Andersson, L., et al., "Hydrolysis of galactolipids by human pancreatic lipolytic enzymes and duidenal contents", Journal of Lipid Research, 1995, vol. 36, pp. 1392-1400.

Andreas Sander, Eberhand Eilers, Andrea Heilemann, Edith von Kreis.Fett/lipid 99 (1997) Nr. 4, 115-120.

Angelino, S.A.G.F., et al., "The first European Symposium on Enzymes and Grain Processing".

An-I Yeh et al., "Effects of Oxido-reductants on rheological properties of wheat flour dough and comparison with some characteristics of extruded noodles", Cereal Chemistry, 1999, vol. 76, No. 5, pp. 614-620.

Archer, David B., et al., "Proteolytic degradation of heterologous proteins expressed in *Aspergillus niger*", Biotechnology Letter, vol. 14, No. 5, May 1992, pp. 357-362.

Arcos J.A. et al, "Quantative Enzymatic Production of 6.O-Acylglucose Esters", Biotechnology and Bioengineering 1998 57(5).

Arpigny Jean Louis et al, "Bacterial lipolytic enzymes: Classification and properties", Biochemical Journal, vol. 343, No. 1, Oct. 1, 1999, pp. 177-183, XP002375631.

August C.A.P.A. et al. "The use of genetic engineering to obtain efficient production of porcine pancreatic phospholipase A2", Biochimica et Biophysica Acta, vol. 1089, 1991, pp. 345-351.

Ausubel, Frederick M., et al., "Short Protocols in Molecular Biology-A Compendium of Methods from Current Protocols in Molecular Biology", 1995, John Wiley & Sons, Inc.

Bachmatova, I., et al., "Lipase of *Pseudomonas mendocina* 3121-1 and its Substrate Specificty", Biologija, 1995.

Balcao V.M., Pavia A.L. Malcata F.X., Enzyme Microb Technhol, May 1, 1996; 18(6):392-416.

Balcao, Victor M and Malcata F. Xavier (1998), Biotechnology Advances, vol. 16, No. 2, pp. 309-341.

Ballance, D.J., et al., "Transformation of *Aspergillus nidulans* by the orotidine-5'-phosphate decarboxylase gene of neurospora crassa", Biochemical and biophysical Research Communications, vol. 112, No. 1, 1983, pp. 284-289.

Ballance, Molecular Industrial Mycology, Systems and Applications for Filamentous Fungi, Leong and Berka (eds.), Marcel Dekker Inc, New York 1991, pp. 1-29.

Barbesgaard, Peder et al Applied Microbiology and Biotechnology (1992) 36: 569-572.

Barnes, P.J., "Lipids in Cereal Technology", Food and Science Technology, Academic Press, 1983.

Basrl, M., et al., "Amidination of Lipase with Hyrdophobic Imidoesters", JAOCS, vol. 69, No. 6, Jun. 1992.

Bateman A and Haft DH (2002) Brief Bioinform 3, 236-245.

Bateman A et al, (2002) Nucleic Acids Res. 30, 276-280.

Bekkers et al, The use of genetic engineering to obtain efficient production of porcine pancreatic phospholipase A2 by *Saccharomyces cerevisiae*, (1991) Biochim Biophys Acta 1089(3), 345-51.

Bengtsson Olivecrona Gunilla et al. Phospholipase activity of milk lipoprotein lipase, Methods in Enzymology, vol. 197, 1991.

Bentley S D et al, Complete genome sequence of the model actinomycete *Streptomyces coelicolor* A3(2), Nature vol. 417, 2002, pp. 141-147.

Berger K.G. (1990) Recent developments in palm oil. In Oleagineux 45:437-443.

Berks, Ben C., "A common export pathway for proteins binding complex redox cofactors?" Molecular Microbiology, 1996, vol. 22, pp. 393-404.

Bilyk, Alexander, et al., "Lipase-catalyzed triglyceride Hydrolysis in Organic Solvent", pp. 320-323, JAOCS, vol. 68, No. 5, May 1991.

Birch et al., "Evidence of Multiple Extracellular Phospholipase Activities of *Aspergillus fumigatus*", Infection and Immunity, Mar. 1996, vol. 64, No. 3, 1996.

Birgitte Hugh-Jensen et al., "Rhizomucor miehei Triglyceride Lipase is Processed and Secreted from Transformed *Aspergillus oryzae*", Lipids, vol. 24, No. 9, 1989.

Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.

Bjorkling, F., et a., "Lipase Catalyzed Organic Synthesis", S. Servie (ed.), Microbial Reagents in Organic Synthesis, pp. 249-260, 1992.

Bjorkling, Frederik, et al., "Lipase Catalyzed Synthesis of PerozycarboxylicAcids and Lipase Mediated Oxidations", Tetrahedron, vol. 48, No. 22, pp. 4587-4592, 1992.

Bjorkling, Frederik, et al., "Lipase -mediated Formation of Peroxycarboxylic acids used in Catalytic Epoxidation of Alkenes", J. Chem. Soc., Chemical Communications, Issue 19, 1990.

Bjurlin et al. Identification of carboxylesterase activities of commercial triacylglycerol hydrolase (lipase) preparations, Eur. J. Lipid Sci. Technol. 104 (2002) 143-155.

Blain JA et al, The Nature of Mycelial Lipolytic enzymes in filamentous fungi, Fems Microbiol. Lett., 1978, vol. 3, 85-87.

Blecker et al, Improved emulsifying and foaming of whey proteins after enzymic fat hydrolysis, (1997) J Food Science, vol. 62, No. 1.

Blumenthal, Cynthia Z., "Production of toxic metabolites in *Aspergillus niger, Aspergillus oryzae*, and *Trichoderma reesei*: justification of mycotoxin testing in food grade enzyme preparations derived from the three fungi", Regulatory Toxicology and Pharmacology, vol. 39, 2004, p. 214-228.

Boel, Esper, et al.; "Rhizomucor miehei Triglyceride Lipase is Synthesized as a Precursor"; Novo Research Institute; vol. 23; No. 7; Jul. 1988.

Bornscheuer U T et al, Trends in Biotechnology, Elsevier Publications, Cambridge GB, vol. 20, No. 10, Oct. 1, 2002, pp. 433-437.

Bornscheuer, Uwe T., Lipase-catalyzed syntheses of monoacylglycerols, Enzyme and Microbiol Technology, vol. 17, pp. 578-586, 1995.

Brady, Leo, et al., "A serine protease triad forms the catalytic centre of a triacylglycerol lipase", Nature, vol. 343, 1990.

Brockerhoff, Hans, et al., "Lipolytic Enzymes", Academic Press, 1974.

Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.

Brzozowski, A.M., et al., "A model for interfacial activation in lipases from the structure of a fungal lipase-inhibitor comples", Nature, vol. 351, 1991.

Buckley J. Thomas et al, Journal of Biological Chemistry, vol. 257, No. 6, pp. 3320-3325, 1982.

Buckley, Biochemistry 1983, 22, 5490-5493.

Bulkacz J et al, Biochim. Biophys. Acta (1981) vol. 664, pp. 148-155.

Bulletin of the IDF 294: 1994.

Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.

Butcher, Bronwyn G., et al., Microbiology, 2002, vol. 148, pp. 3983-3992.

Buxton et al, Gene, 1985, 37:207-214.

Carriere et al, "Pancreatic Lipase Structure- Function Relationships by Domain Exchange", American Chemical Society-Biochemistry (1997), 36, pp. 239-248.

Carriére, Frédéric, et al., "Structural basis for the substrate selectivity of pancreatic lipases and some related proteins", Biochemica et Biophysica Acta, vol. 1376, pp. 417-432, 1998.

Caruthers MH et al (1980) Nuc Acids Res Symp Ser 215-23.

Casimir C A et al Progress in Lipid Research, 2004, pp. 534-552.

Castello, Phillippe, et al., "Effect of exogenous lipase on dough lipids during mixing of wheat flours", Cereal Chemistry, 1998, vol. 75, No. 5, pp. 595-601.

Castello, Phillippe, et al., "Effects of mixing conditions and wheat flour dough composition on lipid hydrolysis and oxidation levels in the presence of exogenous lipase", Cereal Chemistry, 1999, vol. 76, No. 4, pp. 476-482.

Chakravarti DN et al, Biol. Abstracts, 1981, vol. 72, abstract No. 012592.

Cheng Cheng et al., "Transformation of *Trichoderma viride* using the Neurospora crassa pyr4 gene and its use in the expression of a Taka-amylase A gene from *Aspergillus oryzae*", Curr. Genet., 18: 453-456, 1990.

Christensen et al, "A new and simple method to immobilise lipases by means of granulation", 1998 Nachwachsende Rohstoff 10, 98-105.

Christie, William et al., "New Procedures for Rapid Screening of Leaf Lipid Components from Arabidopsis", Phytochemical Analysis, vol. 9, pp. 53-57, 1998.

Christophersen, Claus, et al., "Enzymatic Characterisation of Novamyl a Thermostable α-Amylase", Starch/Sturke, vol. 50, 1998.

Chung O K et al, "Defatted and Reconstituted wheat flours. VI. Response to shortening addition and Lipid Removal in Flours that vary in Bread-making Quality" Cereal Chemistry (1980), vol. 57(2), p111-117.

Chung Ok et al, "Recent Research on Wheat Lipids" Bakers Digest Oct. 1981.

Ciuffreda, Pierangela, et al., "Spectrophotometric Assay of Lipase Activity: A New 40nitrophenyl Ester of a Dialkylglycerol Suitable as a Chromogenic Substrate of Pseudomonas cepacia Lipase", Biocatalysis and Biotransformation, vol. 21, No. 3, pp. 123-127, 2003.

Claesson et al., "Techniques for measuring surface forces", Advances in Colloid and Interface Science, vol. 67, 1996, pp. 119-183.

Clausen, Kim, "New enzyme for degumming", Oils and Fats International, vol. 17, No. 4, Jun. 2001, pp. 24-25.

Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p501-510.

Colombo, Diego, et al., "Optically Pure 1-0- and 3-0-β-D-Glucosylk- and Galactosly-sn-glycerols through Lipase-catalyzed Transformations", Tetrahedron Letters, vol. 36, No. 27, pp. 2865-4868, 1995.

Conference May 6-8, 1999 in Santorini, Greece—Lipases & Lipids Structure, Function and Biotechnological Applications—Slides presented by Charlotte Poulsen.

Cordle et al, "The hydrophobic surface of colipase influences lipase activity at an oil-water interface", Journal of Lipid Research, vol. 39 (1998), 1759-1767.

Coteron, A., et al., "Reactions of Olive Oil and Glycerol over Immobilized Lipases", JAOCS, vol. 75, No. 5, 1998.

Council Directive of Dec. 21, 1988 (89/107/EEC).

Council Regulation (EC) No. 2991/94 May 12, 1994 Official Journal of the European Communities, Sep. 12, 1994, No. L316/2-7.

Creveld, Lucia D, et al., "Identification of Functional and Unfolding Motions of Cutinase as Obtained from Molecular Dynamics Computer Simulations", Proteins: Structure, Function, and Genetics, 33:253-264, 1998.

Cromie, Susan. Psychrotrophs and their Enzyme residues in cheese milk, The Australian Journal of Dairy Technology, vol. 47, Nov. 1992.

Cui et al., "Purification and characterization of an intracellular carboxylesterase from Arthrobacter viscosus NRRL B-1973", Enzyme and Microbial Technology, vol. 24, pp. 200-208, 1999.

Daboussi et al, Heterologous expression of the *Aspergillus nidulans* regulatory gene nirA in Fusarium oxysporum, (1991) Gene 109(1), 155-60.

Daboussi et al., "Transformation of seven species of filamentous fungi using the nitrate reductase gene of *Aspergillus nidulans*", Curr. Genet., 15:453-456, 1989.

Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.

Dalrymple, Brian D., et al., "Three *Neocallimastic patriciarum* esterases associated with the degradation of complex polysaccharides are members of a new family of hydrolases", Microbiology, vol. 142, pp. 2605-2614, 1997.

Danisco, "Unique Chance for Better Bread" *Direct, A Newsletter from Danisco Ingredients* (1996).

Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.

Database accession No. P10480 -& Database UniProt 'Online!, Jul. 1, 1989.

Database accession No. Q44268 -& Database UniProt 'Online! Nov. 1, 1996.

Database accession No. Q9F7Y6 Database UniProt 'Online!, Mar. 1, 2001.

Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales De Technologie Agricole, vol. 28, No. 4, 1979, pp. 445-468.

Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.

Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.

Database UNIPROTKB Jun. 1, 2003, S. Omura et al: "putative secreted hydrolase from *Streptomyces avermitilis*" XP002376340 retrieved from EBI, Hinxton, UK Database accession No. Q828T4 abstract.

Database UNIPROTKB May 1, 2000, S.D. Bentley et al: "Putative Secreted Hydrolase from *Streptomyces coelicolor*" XP002376339 retrieved from EBI, Hinxton, UK Database accession No. Q9S2A5 abstract.

Davies, Progress in Industrial Microbiology, Martinelli and Kinghorn (eds.), Elsevier, Amsterdam 1994, 29:525-560.

De Haas GH et al, "Purification and Properties of Phospholipase A from Porcine Pancreas" Biochim. Biophys. ACTA, 1968, vol. 139, pp. 103-117.

Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.

Dellaporta, et al.; "A Plant DNA Minipreparation Version II"; Plant Molecular Biology Reporter(1983); vol. 1(4); pp. 19-21.

Derewenda et al, "The crystal and molecular structure of the Rhizomuxor miehei Triacylglyceride Lipase at 1•9 Å Resolution", J. Mol. Biol. 1992, 227:818-839.

Derewenda, Urszula, et al., "Catalysis at the Interface: The Anatomy of a Conformational Change in a Triglyceride Lipase", Biochemistry, vol. 31, pp. 1532-1541, 1992.

Direct, A Newsletter from Danisco Ingredients, Sep. 1996.

Directive 2000/36/EC. Http://europa.eu.int/scadplus/leg/en/lvb/121122b.htm. Dato: 16.06.04.

Drost-Lustenberger, Cornelia, et al., "Lipopan F BG-application and mechanism of a new lipase for bread baking", Cereal Food, 2003.

Drost-Lustenberger, Cornelia, et al., "Lipopan F BG-unlocking the natural strengthening potential in dough", Cereal Food, 2004.

Duan, Rui Dong, Fat Digestion and Absorption (2000), p. 25-46, publisher AOCS Press, Champaign III CODEN 69ACBA Conference; general review written in English.

Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.

Ducancel, Frederic, et al., "Complete amino acid sequence of a PLA2 from the tiger snake *Notechis sculatus* scutatus as deduced from a complementary DNA", Nucleic Acids Research, vol. 16, No. 18, 1988.

Dugi Ka et al, "Human hepatic and lipoprotein lipase: the loop covering the catalytic site mediates lipase substrate specificity", Journal of Biological Chemistry (1995), vol. 270, pp. 25, 396-pp. 25, 401.

Dutilh & Groger, "Improvement of Product Attributes of Mayonnaise by Enzymic Hydrolysis of Egg Yolk with Phospholipase A2", 1981 J. Sci. Food Agric. 32, 451-458.

Eddine et al, "Cloning and expression analysis of NhL1, a gene encoding an extracellular lipase from the fungal pea pathogen *Nextria haematococca* MP VI (*Fusarium solani* f. sp. pisi) that is expressed in planta", Mol. Genet. Genomics (2001) 265: 215-224.

EFEMA Index of Food Emulsifiers Jan. 2004, 4th Edition.

Ellaiah et al., "Production of lipase by immobilized cells of *Aspergillus niger*", Process Biochemistry, vol. 39, 2004, pp. 525-528.

Elyk, Alexander, et al., "Lipase-Catalyzed—", JAOCS, vol. 08, No. 5, May 1991, pp. 320-323.

Engelhorn and Raab, "Rapid Electroblotting of Small DNA Fragments from Polyacrylamide Gels", Biotechniques (1991) 11(5):594-6.

Engelhorn et al., "Rapid Electroblotting of Small DNA Fragments from Polyacrylamide Gels"; Biotechniques(1991); vol. 11(5); pp. 594-596.

Enzymes in food processing (3rd Ed.), Academic press 1993.

EPO, Mobay Chemical Corporation—Decision of the Technical Board of Appeal 3.3.1 dated Jul. 1, 1982, *Official Journal EPO*, Oct. 1982, pp. 394-402.

Ettinger, William F. et al., "Structure of Cutinase Gene, cDNA, and the Derived Amino Acid Sequence from Phytopathogenic Fungi", Biochemistry, vol. 26, pp. 7883-7892, 1987.

Euromonitor International, "The World Market for Dairy Products—Introduction, Executive Summary, Operating Environment, World Market Overview, Key Trends and Developments" in *Euromonitor, Strategy 2000*, Feb. 2001.

European Parliament and Council Directive No. 95/2/EC of Feb. 20, 1995 on food additives other than colours and sweeteners.

European Parliament and Council Directive No. 98/72/EC of Oct. 15, 1998 amending Directive 95/2/EC on food additives other than colours and sweeteners.

Eurpean Journal of Biochemistry, vol. 166, 1987, Published by Springer International on behalf of the Federation of European Biochemical Societies.

Ezra, David, et al., "Coronamycins, peptide antibiotics produced by a verticillate Streptomyces sp. (MSU-2110) endophytic on Monstera sp.", Microbiology, 2004, vol. 150, p. 785-793.

Fauvel, et al.; "Purification of Two Lipases With High Phospholipase A, Activity from Guinea-Pig Pancreas"; Biochimica et Biophysica Acta(1981); vol. 663; pp. 446-456.

Fernandez-Garcia et al., "The use of lipolytic and proteolytic enzymees in the manufacture of manchego type cheese from ovine and bovine milk", 1994 J. Dairy Sci. 77: 2139-2149.

Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.

Ferrer et al, 2000, J. Chem. Technol. Biotechnol. 75, 569-576.

Finizym Technical Information, Novo Enzymes, 1981.

Fødevarenubusteriet (2003). Bekendtgørelse om indhold af transfedtsyrer I olier og fedtstoffer. Bekendtgørelse nr. 160 af Nov. 3, 2003.

Forman, Todd, "Enzymes Used in Bread Baking: An Application Update", Technical Bulletin, vol. XXVI, Issue 10, Oct. 2004.

Fox, et al.; "Isolation and some Properties of Extracellular Heat-Stable Lipases: from *Pseudomonas Fluorescens* Strain AFT 36"; Journal of Dairy Research (1988); vol. 50, pp. 77-89.
Frenken N. et al (1992) Appl. Envir. Microbiol. 58 3787-3791.
Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.
Fugman, Douglas A et al Biochemica et Biophysica acia 795 (1984) 191-195.
Galliard T and Dennis S (1974) Phytochemistry vol. 13, pp. 1731-1735.
Galliard, "The Enzymic Breakdown of Lipids in Potato Tuber by Phospholipid- And Galactolipid- Acyl Hydrolase Activities and by Lipoxygenase", Phytochemistry, 1970, vol. 9, pp. 1725-1734.
Gan, Z. et al., "Rapid Communication- Antisera agains: Wheat Diacylgalactosylglycerol (MGDG) and Diacyldigalactosylglycerol (DGDG)", Journal of Cereal Science, vol. 18, pp. 207-210, 1993.
Ganghro AB & Dahot MU, Sci Int. (Lahore), 1992, vol. 4, pp. 169-172.
Gemel, Joanna et al., "Comparison of galactolipase activity and free fatty acid levels in chloroplasts of chill-sensitive and chill resistant plants", European Journal of Biochemistry, vol. 166, 1987.
Geus et al (1987) Nucleic Acids Research 15(9) p3743-3759.
Gilbert, E. Jane, et al., "Purification and properties of extracellular lipase from *Pseudomonal aeruginosa* EF2", Journal of General Microbiology, 1991, vol. 137, pp. 2223-2229.
Gillian, B., Turgeon et al., "*Cochliobolus heterostrophus* using the *Aspergillus nidulans* amdS gene", Mol Gen Genet, 201: 450-453, 1985.
Goodey et al, Yeast Biotechnology, Berry et al (eds.), Allen and Unwin, London 1987, pp. 401-429.
Graille J, Lipid Technology, vol. 5, No. 1, 1993, pp. 11-16.
GRAS Notification dated Apr. 11, 2001 by Novozymes for Lecitase$^R$ and Lipopan ™ F.
Greenough et al (1996) Food Chem Toxicology 34:161-166 and PubMed abstract in respect thereof.
Greenough R J et al, Food and Chemical Toxicology, vol. 34(2), 1996, pp. 161-166.
Haas and Berka, 1991, Gene, 109:107-113.
Haas, et al., "Enzymatic Phosphatidylcholine Hydrolysis in Organic Solvents: An Examination of Selected Commercially Available Lipases", JAOCS, vol. 71, No. 5, May 1994, pp. 483-490.
Haas, et al.; "Lipases of the Genera *Rhizopus* and *Rhizomucor*. Versatile Catalysts in Nature and the Laboratory"; Food Biotechnology Micro-organisims (1995); pp. 549-588.
Haggag H F et al. Egypt J Food Sci vol. 22, No. 1 pp. 99-107 (1994).
Hansen, Chr., Danisco and Novozymes, Apr. 3, 2002, Food Ingredients day, R&D—the main ingredients for growth.
Hara, et al.; "Comparative Study of Comercially Available Lipases in Hydrolysis Reaction of Phosphatidylcholine", JAOCS (1997); vol. 74; No. 9, pp. 1129-1132.
Hawker, Kim L., et al., "Heterologous expression and regulation of the Neurospora crassa nit-4 pathway-specific regulartory gene for nitrate assimilation in *Aspergillus nidulans*", Gene., vol. 100, pp. 237-240, 1991.
Helmsing, "Purification and Properties of Galactolipase", Biochim., Biophys., Acta, vol. 178, pp. 519-533, 1969.
Henderson, H.E., et al., "Structure-function relationships of lipoprotein lipase: mutation analysis and mutagenesis of the loop region", Journal of Lipid Research, vol. 34, 1993, pp. 1593-1602.
Henke, Erik, et al., "Activity of Lipases and Esterases towards Tertiary Alcohols: Insights into Structure-Function Relationships", Angew. Chem. Int. Ed., 2002, vol. 41, No. 17.
Hernquist L & Anjou K (1993) Diglycerides as a stabilizer of the β'-crystal form in margarines and fats, in Fette Seifen Anstrichmittel 2:64-66.
Hernquist L. Herslof B. Larsson K & Podlaha O. (1981) Polymorphism rapeseed oil with low content of erucic acid and possibilities to stabilize the β'-crystal form in fats, in Journal of Science and Food Agriculture 32:1197-1202.
Hilton S et al, Biochemistry vol. 29, No. 38, 1990, pp. 9072-9078.
Hilton S, Buckley JT, J Biol Chem. Jan 15, 1991; 266(2): 997-1000.
Hirayama O et al, Biochim Biophys Acta. 1975, vol. 384(1), p127-37.
Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.
Höfelmann et al, J. Food Sci., 1985, 50:1721-1731.
Holmquist et al., "Lipases from *Rhizomucor miehei* and *Humicola lanuginosa*: Modification of the Lid covering the active site alters enantioselectivity", Journal of Protein Chemistry, vol. 12, No. 6, 1993.
Holmquist et al., "Probing a Functional Role of Glu87 and Trp89 in the Lid of *Humicola lanuginosa* Lipase through Transesterification Reactions in Organic Solvent", Journal of Protein Chemistry, 1995, vol. 14, No. 4, pp. 217-224.
Holmquist et al., "Trp89 in the Lid of *Humicola lanuginosa* Lipase is Important for Efficient Hydrolysis of Tributyrin", Lipids, vol. 29, No. 9, 1994.
Horn T et al, (1980) Nuc Acids Res Symp Ser 225-232.
Hoshino, et al.; "Calcium Ion Regulates the Release of Lipases of *Fusarium oxysporum*"; J. Biochem (1991); vol. 110; pp. 457-461.
Hoshino, et al.; "Purification and Some Characteristics of Extracellular Lipase from *Fusarium oxysporum f. sp. lini*"; Biosci. Biotech. Biochem (1992); pp. 660-664.
Hoshino, Tamotsu, et al., "Purification and Some Characteristics of Extracellular Lipase from *Fusarium oxysporum*", Biosci. Biotech. Biochem., vol. 56, No. 4, pp. 660-664, 1992.
Hossen, Monjur and Hernandez, Ernesto, Lipids, vol. 39, Aug. 2004, pp. 777-782.
Hou Ching T, Journal of Industrial Microbiology, vol. 13, No. 4, 1994, pp. 242-248.
Hübner et al., "Interactions at the lipid-water interface", Chemistry and physics of Lipids, vol. 96, 1998, pp. 99-123.
Hugh-Jensen, Birgitte, et al., "*Rhizomucor miehei* Triglyceride Lipase is Processed and Secreted from Transformed *Aspergillus oryzae*", Lipids, vol. 24, No. 9, 1989.
Icard-Verniere, Christele, et al., "Effects of mixing conditions on pasta dough development on biochemical changes", Cereal Chemistry, 1999, vol. 76, No. 4, pp. 558-565.
Igrejas, Gilberto, et al., "Genetic and Environmental Effects on Puroindoline-a and Puroindoline -b Content and their Relationship to Technological Properties in French Bread Wheats", Journal of Cereal Science, vol. 34, 2001, pp. 37-47.
Ikeda H et al, Nature Biotech, vol. 21, 2003, p. 526-531.
Industrial enzymology (2nd Ed.), The Macmillan press 1996.
Ishihara et al Biochimica et Biophysica Acta 388 (1975) 413-422.
Isobe and Nokihara, Febs. Lett., 1993, 320:101-106.
Isobe K et al, Journal of Molecular Catalysis B: Enzymatic 1 (1995), pp. 37-43.
Iwai and Tsujisaka (in Lipases, Borgström and Brockman (eds.), Elsevier, Amsterdam, 1984, pp. 443-468.
Izco et al. Adv Food Sci vol. 21 N 3/4, (10-116) 1999.
Jacob, Jules S., et al., "The Effects of Galactolipid Depletion on the Structure of a Photosynthetic Membrane", The Journal of Cell Biology, vol. 103, Oct. 1986, pp. 1337-1347.
Jacobsberg B. & Oh C.H. (1976) Studies in Palm Oil Crystallisation, in Journal of the American Oil Chemist Society 53:609-616.
jan-Willem F. A. Simons et al., "Cloning, purification and characterisation of the lipase from *Staphylococcus epidermidis*", Eur. J. Biochem., vol. 253, pp. 675-683, 1998.
Jeng-yen Lin, Matthew, "Wheat Polar Lipids- A Theseis Submitted to the Graduate Faculty of the North Dakota State University of Agriculture and Applied Science", May 1972.
Joerger et al., "Alteration of Chain Length Selectivity of a *Rhizopus delemar* Lipase through Site-Directed Mutagenesis", Lipids, vol. 29, No. 6, 1994, pp. 377-384.
Jong et al.; "American Type Culture Collection Catalogue of Filamentous Fungi"; Eighteenth edition (1991).
Joshi, et al.; "Specificity of Fungal Lipase in Hydrolytic Cleavage of Oil"; Acta Microbiologica Hungarica (1987); vol. 34(2); pp. 111-114.
Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.

Jurgens, Catharina, et al., "Directed evolution of a (βα)8-barrel enzyme to catalyze related reactions in two different metabolic pathways", PNAS, Aug. 29, 2000, vol. 97, No. 18, pp. 9925-9930.
Kaniuga Z, Acta Biochim Pol. (1997), vol. 44(1), p21-35.
Kapur J & Sood ML, J. Parasit., 1986, vol. 72, pp. 346-347.
Kasai, Naoya, et al., "Chiral C3 epoxides and halophydrins: Their preparation and synthetic application", Journal of Molecular Catalysis B: Enzymatic, vol. 4, 1998, pp. 237-252.
Kawamura and Doi, J. of Bacteriology Oct. 1984, p442-444.
Keller, R.C.A., et al., "Competitive Adsorption Behaviour of Wheat Flour Components and Emulsifiers at an Air-Water Interface", Journal of Cereal Science, vol. 25, 1997, pp. 175-183.
Keum J S et al. Korean J Dairy Sci 15 (2): 103-117 1993.
Kim, Hyung Kwoun, et al., Expression and characterization of Ca2+-independent lipase from *Bacillus pumilus* B26, Biochimica et Biophysica Acta, vol. 1583, 2002, pp. 205-212.
Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.
Kimura, Yoshiharu, et al., "Application of Immobilized Lipase to Hydrolysis of Triacylglyceride", Eur J. Appl Microbiol Biotechnol, 1983, vol. 17, pp. 107-112.
King et al, Molecular and Cell Biology of Yeasts, Walton and Yarronton (eds.), Blackie, Glasgow, 1989, pp. 107-133.
Kirk, Ole, et al., "Fatty Acid Specificity in Lipase-Catalyzed Synthesis of Glucoside Esters" Biocatalysis, 1992, vol. 6, pp. 127-134.
Klein, Robert R., et al., "Altered Acyl Chain Length Specificity of *Rhizopus delemar* Lipase Through Mutagenesis and Molecular Modeling", Lipids, 1997, vol. 32, No. 2, pp. 123-130.
Klein, Robert R., et al., "Additive Effects of Acyl-Binding Site Mutations on the Fatty Acid Selectivity of *Rhizopus delemar* Lipase", JAOCS, vol. 74, No. 11, 1997.
Kocak et al, Milchwissenschaft 51(1), 1996.
Kochubei et al Role of lipids in the organization of the closest surroundings of the reaction centers(1976) Institute of Plant Physiology.
Kochubei S M et al, Biophysics (1981), vol. 26(2), p299-304.
Kochubei S M et al, Mol Biol (Mosk) (1975), vol. 9(2), (p190-3) p150-153.
Kochubei SM et al, Mol Biol (Mosk) (1978),(vol. 1, p. 47-54) p32-37.
Kolkovski et al (1991) Fish Nutrition in Practice, Biarritz (France), Jun. 24-27.
Kostal, Jan, et al., "Enhanced Arsenic Accumulation in Engineered Bacterial Cells Expressing ArsR", Applied and Environmental Microbiology, Aug. 2004, pp. 4582-4587.
Kouker, et al.; "Specific and Sensitive Plate Assay for Bacterial Lipases"; Applied and Environmental Microbiology (1987); vol. 53(1); pp. 211-213.
Krishna, Sajja Hari, et al., "Enantioselective transesterification of a tertiary alcohol by lipase A from *Candida antarctica*", Tetrahedron: Asymmetry, vol. 13, 2002, pp. 2693-2696.
Kristensen A.C.J. (2004) Preparation of margarine and spreads by enzyme-generated emulsifiers. Master thesis, The Royal Veterinary and Agricultural University, Frederiksberg, Copenhagen.
Krog, Cereal Foods World, The American Association of Cereal Chemists, p. 10, Jan. 1979, vol. 24, No. 1, pp. 10-11.
Krupa, Zbigniew et al., "Requirement of Galactolipids for Photosystem J Activity In Lyophilized Spinach Chloroplasts", Biochimica et Biophysica Acta, 408, pp. 26-34, 1975.
Kuipers, Oscar P., et al., "Enhanced Activity and Altered Specificity of Phospholipase A2 by Deletion of a Surface Loop", Science, vol. 244, 1989.
Nerland A.H., "The Nucleotide Sequence of the Gene Encoding GCAT from *Aeromonas salmonicida* SSP. *Salmonicida*", Journal of Fish Diseases, 1996, vol. 19, No. 2, pp. 145-150, XP008049669.

Nerland A. H., "Glycerophospholipid-cholesterol acyltransferase percursor", SwissProt, Feb. 11, 2005, XP002318368.
Buckley J. Thomas, "Substrate specificity of bacterial glycerophospholipid Cholesterol Acyltransferase", Biochemistry, 1982, vol. 21, pp. 6699-6703.
U.S. Appl. No. 60/083,277, filed Apr. 28, 1998, Spendler et al.
AOCS Introduction to the Processing of Fats and Oils, American Oil Chemists Society (2003) p. III-16 to III-19.
Briand, et al., Substrate Specificity of the Lipase from Candida Parapsilosis, Lipids (1995) vol. 30, No. 8, p. 747-754.
Chica, et al., Semi-rational Approaches to Engineering Enzyme Activity: Combining the Benefits Of Directed Evolution And Rational Design, Current Opinion in Biotechnology (2005) vol. 16, p. 378-384.
Sequence of Enzyme GCAT: Accession No. P10480 found at http://www.ncbi.nlm.nih.gov/entrez/viewer.fcgi?db=protein&id=118572649.
Garzillo, et al., Production, Purification and Characterization of Glucose Oxidase from Penicillium Variabile P16[1], Biotechnol. Appl. Biochem. (1995) vol. 22, p. 169-178.
International Dairy Federation Bulletin Document 1979, Document 116, Definition of Recombined Milk.
Seffernick, et al., Melamine Deaminase and Atrazine Chlorohydrolase: 98 Percent Identical but Functionally Different, Journal of Bacteriology (2001) vol. 183, No. 8, p. 2045-2410.
Seino, et al., Enzymatic Synthesis of Carbohydrate Esters of Fatty Acid (1) Esterification of Sucrose, Glucose, Fructose and Sorbitol, JAOCS, (1984) vol. 61, No. 11, p. 1761-1765.
Sen, et al., Developments in Directed Evolution for Improving Enzyme Functions, Appl. Biochem. Biotechnol (2007) vol. 143, No. 3, p. 212-223.
Stryer, L. (1981) Biochemistry $2^{nd}$ Ed. W. H. Freeman and Co. San Francisco.
Witkowski, et al., Conversion of a β-Ketoacyl Synthase to a Malonyl Decarboxylase by Replacement of the Active-Site Cysteine with Glutamine, Biochemistry (1999) vol. 38, p. 11643-11650.
Garcia, et al., 1,2-Diacyl-sn-glycerol: Sterol Acyl Transferase from Spinach Leaves (*Spinacia olerecea L.*), Methods of Enzymology (1981) vol. 71, p. 768-772.
Verenium Corporation leaflet Purifine® Enzyme Jan. 2008.
Aust K., "Applications of lecithin in bakery foods", AIB Research Technical Bulletin, vol. XV, Issue 12, Dec. 1993, 1-6.
Si and Lustenberger. "Novamyl®—a true anti-staling enzyme A-06565" Novo Nordisk. A presentation published at IFIA in Japan and at the meeting at IATA in Valencia, Spain, May 1998.
"Enzyme catalyzed synthesis of structured phospholipids with conjugated linoleic acid and plant sterols." A Dissertation by MD. Monjur Hossen, May 2005.
Mustranta et al., "Comparison of lipases and phospholipases in the hydrolysis of phospholipids". Process Biochemistry 30(5):393-401, 1995.
Cereal Foods World, American Association of Cereal Chemists, Sep. 1983, 28(9), p. 561.
Poldermans, B. and Schoppink, P., "Controlling the Baking Process and Product Quality with Enzymes", Cereal Foods World, Mar. 1999, 44(3), 132-135.
Si J.Q, "New Enzymes for the baking industry", Food Tech Europe, Mar./Apr. 1996, 3:60-64.
Leon et al., "A new approach to study starchy changes occurring in the dough-baking process and during bread storage" Z Lebensm Unters Forsch A (1997) 204: 316-320.

* cited by examiner

SEQUENCE LISTING

```
<160> NUMBER OF SEQ ID NOS: 3

<210> SEQ ID NO 1
<211> LENGTH: 25
<212> TYPE: PRT
<213> ORGANISM: Artificial Sequence
<220> FEATURE:
<223> OTHER INFORMATION: general sequence of polypeptide in glycosylated
      or non-glycosylated form capable of exhibiting lipase activity
<220> FEATURE:
<221> NAME/KEY: MISC_FEATURE
<222> LOCATION: (22)..(22)
<223> OTHER INFORMATION: Xaa is any amino acid

<400> SEQUENCE: 1

Ser Val Ser Thr Ser Thr Leu Asp Glu Leu Gln Leu Phe Ala Gln Trp
1               5                   10                  15

Ser Ala Ala Ala Tyr Xaa Ser Asn Asn
            20                  25
```

```
<210> SEQ ID NO 2
<211> LENGTH: 7
<212> TYPE: PRT
<213> ORGANISM: Artificial Sequence
<220> FEATURE:
<223> OTHER INFORMATION: general sequence of polypeptide in glycosylated
      or non-glycosylated form capable of exhibiting lipase activity

<400> SEQUENCE: 2

Val His Thr Gly Phe Trp Lys
1               5

<210> SEQ ID NO 3
<211> LENGTH: 14
<212> TYPE: PRT
<213> ORGANISM: Artificial Sequence
<220> FEATURE:
<223> OTHER INFORMATION: general sequence of polypeptide in glycosylated
      or non-glycosylated form capable of exhibiting lipase activity

<400> SEQUENCE: 3

Ala Trp Glu Ser Ala Ala Asp Glu Leu Thr Ser Lys Ile Lys
1               5                   10
```

FOODSTUFF

RELATED APPLICATIONS

This application is a divisional application of U.S. application Ser. No. 09/750,990, filed Dec. 28, 2000, which is the continuation-in-part of PCT/IB99/01354, filed Jul. 20, 1999, designating the U.S. and published as WO 00/05396, with claims of priority from Great Britain application nos. 9815905.6, filed Jul. 21, 1998 and 9824758.8, filed Nov. 11, 1998.

All of the foregoing applications, as well as all documents cited in the foregoing applications ("application documents") and all documents cited or referenced in application documents are hereby incorporated herein by reference. Also, all documents cited in this application ("herein cited documents") and all documents cited or referenced in herein cited documents are hereby incorporated herein by reference.

The present invention relates to a foodstuff. More particularly, the present invention relates to a foodstuff comprising at least one functional ingredient which has been generated in situ by a conversion agent.

Traditionally food was prepared in the private households and the constituents of the food or of the foodstuff were brought to the kitchen of the household where the food or foodstuff was prepared shortly before consumption.

Industrial development increased the demand for the reduction of the time and effort required to prepare food or foodstuffs. Thus there has been a massive expansion in the industrial preparation of food.

Recently, there has been increased demand for improvements in the quality of industrially prepared food. In particular there is demand for improved taste, eating quality and shelf life. In an attempt to address these demands for improved foodstuffs, industrial food producers have utilised and have relied upon functional ingredients to meet the demands for quality and shelf life. Functional ingredients such as emulsifiers, hydrocolloids, preservatives, antioxidants, colourings and flavourings are widely used in the food industry.

More recently, there has been demand from consumers to reduce the number of additives, such as functional ingredients, included in foodstuffs. Thus, there is a desire to prepare industrially foodstuffs meeting the quality requirements of consumers whilst minimising the number of additives in the final foodstuffs.

Both Douglas B. Sarney et al., Enzymatic Synthesis of Sorbitan Esters Using a Low-Boiling-Point Azeotrope as Reaction Solvent, Biotechnology and Bioengineering, 1997 vol. 54(4) and J. A. Arcosm et al., Quantitative Enzymatic Production of 6.O-Acylglucose Esters, Biotechnology and Bioengineering 1998 57(5), teach the use lipase for the production of emulsifiers. The teachings require the synthesis of emulsifiers in an organic solvent system. The emulsifier is then isolated from the organic solvent system before use in food.

A. Coteron et al., Reactions of Olive Oil and Glycerol over Immobilised Lipases, JAOCS, Vol. 75, no. 5 (1998) reports the use of immobilised lipase in the reaction of olive oil and glycerol. Subsequent to the reaction the immobilised lipase is removed from the reaction mixture.

JP-A-90188214 reports the use of an immobilised lipase for the hydrolysis and ester exchange of triglyceride. In this process part of the triglyceride is partially hydrolysed to free fatty acid. The partially hydrolysed triglyceride product is used for production of margarine.

U.S. Pat. No. 5,288,619 relates to enzymatic methods for the production of oils or fats having a specific fatty acid profile. In particular, U.S. Pat. No. 5,288,619 discloses the use of a lipase to transesterification two oils or fats. A particularly preferred embodiment of this document uses an immobilised lipase. The resultant oils or fats, the required specific fatty acid profile, may subsequently be incorporated in a foodstuff or food material. For example the transesterified oils/fats may be incorporated in a margarine recipe.

U.S. Pat. No. 4,865,866 teaches the use of a lipase to rearrange by transesterification the fatty acids components of a fat/oil. The disclosed lipases are immobilised, for example by support on Celite. The process is performed to provide a fat/oil composition having a specific fatty acid distribution. The fat/oil composition obtained by the transesterification may be incorporated in a foodstuff such as a plastic emulsion product e.g. a margarine or low fat spread.

JP-A-5211852 discloses the addition of a lipase to a mixture of water and less than 30% oil. The product prepared in this method may be used in the production of mayonnaise. The mayonnaise is prepared at a temperature such that the activity of lipase is not reduced. In the procedure of JP-A-5211852 the oil is degraded to free fatty acid or fatty acid salts(soap) and glycerol which may provide the emulsifying properties. However, this may be problematic as the emulsification properties of this reaction product will depend on the pH of the mixture. This is because the effect of fatty acid is pH dependent. At low pH free fatty acid is present in the acid form which has low emulsification properties. At alkaline pH however free fatty acid is available as a soap, which is known to have good emulsification properties. For the production of a creamy substance described in JP-A-5211852 this may not be a problem. However, for other foodstuffs this may be a problem. For example, in margarine production pH is adjusted to 4.5 or 5.5 or other pH values depending on the recipe. In this case the effect of free fatty acid formation by the lipase will impact on the emulsification of the foodstuff.

The present invention addresses the problem of the prior art

Figure 1:
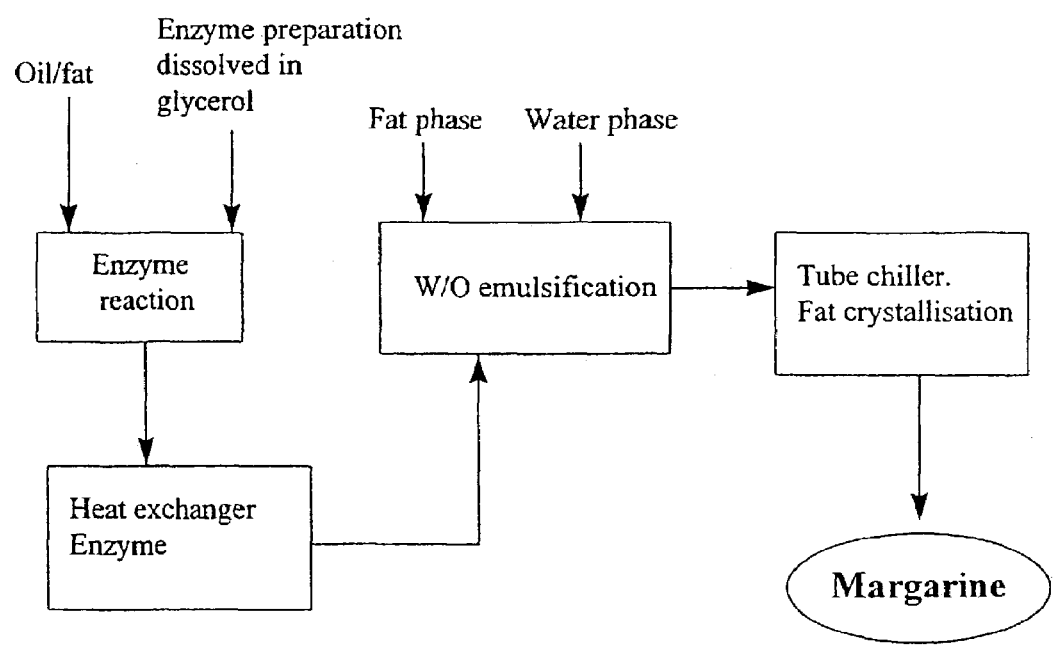
FIG. 1 is a flow diagram for in situ production of emulsifier.

According to a first aspect of the present invention there is provided use of a conversion agent to prepare from a food material a foodstuff comprising at least one functional ingredient, wherein the at least one functional ingredient has been generated from at least one constituent of the food material by the conversion agent.

According to a second aspect of the present invention there is provided a process for preparing a foodstuff comprising the steps of (i) providing a food material; (ii) contacting the food material with a conversion agent such that a functional ingredient is generated by the conversion agent from at least one constituent of the food material.

According to a third aspect of the present invention there is provided a foodstuff prepared from a food material, wherein the foodstuff comprises at least one functional ingredient, and wherein the at least one functional ingredient has been generated from at least one constituent of the food material by a conversion agent.

By the term "functional ingredient" we mean a constituent of the foodstuff which performs a specific function in the foodstuff. Preferably by the term "functional ingredient" we mean an emulsifier, hydrocolloid, preservative, antioxidant, colouring, flavouring, and/or viscosity modifier. Preferably by the term "functional ingredient" we mean a constituent of the foodstuff which has one or more of surface active properties, antioxidative effect, anti-bacterial effect including bacteriostatic effect and/or bactericidal effect and viscosity modifying effect, preferably viscosity improving effect.

By the term "foodstuff" we mean a substance which is suitable for human or animal consumption.

The above aspects of the present invention are advantageous as they overcome the problems associated with the prior art.

The present invention utilises a conversion agent, such as enzyme, during the production of a foodstuff to generate one or more functional ingredients, for example emulsifiers, antioxidants or preservatives, from a constituent of a food material (i.e. ingredients) from which the foodstuff is prepared. The constituent(s) may be a fat, for example. Thus, instead of adding food additives produced by traditional chemical synthesis, the present invention provides for the in situ synthesis of a required functional ingredient.

Traditional chemical synthesis of functional ingredients is problematic because syntheses are often carried out under extreme conditions, such as high temperatures (e.g. ~200° C.). Under extreme conditions, side reactions may occur. Thus, although the resultant product may be substantially pure, it may contain undesirable components. To eliminate undesirable components, reactions must be closely controlled and/or the resultant product may require purification, adding to a production process. The present invention aims to overcome these disadvantages.

Moreover, by generating the functional ingredient from at least one constituent of the food material using a conversion agent, the foodstuff comprises at least one less "additive" material. This is advantageous because of the improvement in the ease of production. Moreover, the foodstuff may contain less "additives". The reduction or elimination of "additives" is desirable to consumers and inclusion of additives often must be declared to the consumer in the ingredients listing on the foodstuff. Thus, the present invention is further advantageous.

As one of the advantages of the present invention is the possibility of providing a foodstuff prepared from a food material and comprising a functional ingredient which has been generated from a constituent of the food material, the following two aspects are preferred embodiments of the present invention in one preferred aspect the food material is substantially free of one of the at least one functional ingredients. In this aspect one of the functional ingredients must have been prepared at least in part in accordance with the present invention. By the term "substantially free" we mean the amount of the functional ingredient present in the food material is less than 10% of the amount of the same functional ingredient present in the foodstuff, more preferably less than 5%, more preferably less than 2%. more preferably less than 1%, yet more preferably less than 0.5% in a further preferred aspect substantially all of at least one of the functional ingredients present in the foodstuff has provided by conversion in accordance with the present invention, together optionally with any of the functional ingredient present in the food material. By the term "substantially all" we mean the amount of the functional ingredient present in the foodstuff provided by conversion in accordance with the present invention, together optionally with any of the functional ingredient present in the food material, is greater than 90% of the total amount of the functional ingredient, more preferably greater than 95%, more preferably greater than 98%, more preferably greater than 99%.

The food material may be contacted with the conversion agent in any manner. The food material may be contacted with the conversion agent in an immobilised form. The food material may simply be added to the conversion agent or vice versa. In the latter aspect, the conversion agent may be subsequently removed from the food material/foodstuff or may remain in the food material/foodstuff. In a preferred aspect the conversion agent is present in the foodstuff.

The above preferred aspect is advantageous because one may contact the food material with the conversion agent to thereby provide a foodstuff suitable for consumption. No further processing or addition of ingredients may be required; a foodstuff comprising a required functional ingredient is produced. Thus a foodstuff may be provided in which a required functional ingredient has been simply generated. Synthesis of the functional ingredient discretely from the foodstuff followed by subsequent addition is not required. Moreover, provided of course the conversion agent is suitably chosen so that it is compatible with a foodstuff i.e. it is edible, further processing of the foodstuff may not be necessary. However, the present invention encompasses foodstuffs which have been further processed.

Preferably, the conversion agent is a catalyst.

In a preferred aspect, the conversion agent is an enzyme. This aspect is particularly preferred because enzymes are readily available, may be chosen to convert a specific constituent of the food material and/or may be chosen to generate a specific functional ingredient. Yet further, enzymes may be denatured by heat. Thus in a further preferred aspect, the foodstuff/food material is heated after generation of the functional ingredient. The enzyme will be denatured and may then constitute protein. This is advantageous because the denatured enzyme need not be declared on the foodstuff/food material ingredients.

The use of enzymes is advantageous because denatured enzymes are considered, particularly under food labelling regulations, to constitute a processing aid. Inactivated enzymes are not considered to be additives; the addition of additives to foodstuffs is undesirable to many consumers.

Inactivation of the conversion agent, in particular denaturation of the enzyme, is advantageous because it allows one to control the amount of functional ingredient generated. For example, the generation of the functional ingredient may be monitored (for example by measurement of the functional properties of the food material) or the rate thereof determined. One may then terminate the generation of the functional ingredient, when a suitable amount of functional ingredient has been generated, by heating the food material. Thus the amount of the functional ingredient and the properties of the food material/foodstuff may easily be controlled.

Preferably, the enzyme is selected from lipases (EC 3.1.1.3), esterases, amylases, xylanases, proteases, lyases, including glucan lyases and α-1,4-glucan lyase, derivatives and mixtures thereof. More preferably, the enzyme is selected from lipases, esterases, derivatives and mixtures thereof.

Preferably the enzyme is an enzyme as described in and/or as claimed in Danish Patent Application No. 0400/97. IN other words preferably the enzyme is a polypeptide in glycosylated or non-glycosylated from capable of exhibiting lipase activity wherein the polypeptide comprises at least one amino acid sequence selected from the group consisting of (I)   Ser-Val-Ser-Thr-Ser-Thr-Leu-Asp-Glu-Leu-Gln-Leu-Phe-Ala-Gln-Trp-Ser-Ala-Ala-Ala-Tyr-Xaa-Ser-Asn-Asn (SEQ ID NO: 1)

(II) Val-His-Thr-Gly-Phe-Trp-Lys (SEQ ID NO: 2)

(III) Ala-Trp-Glu-Ser-Ala-Ala-Asp-Glu-Leu-Thr-Ser-Lys-Ile-Lys (SEQ ID NO: 3)

where Xaa represents an amino acid selected from the group consisting of Ala, Arg, Asn, Asp, Cys, Gln, Glu, Gly, His, Ile, Leu, Lys, Met, Phe, Pro, Ser, Thr, Trp, Tyr and Val.

In a further aspect the enzyme may be an enzyme as described in and/or as claimed in International Patent Application No. PCT/IB98/00708, filed 6 May 1998.

Preferably, the enzyme is isolated from a plant (preferably soy bean, rice bran, corn, rapeseed, peanut, pineapple, potato, oat, wheat and/or sunflower seed), an animal (preferably an animal pancreas) or a micro-organism. Preferably, the microorganism selected from *Aspergillus niger, Rhizopus delemar, Rhizopus arrhizus, Mucor miehei, Pseudomonas* sp., *Candida rugosa, Pencilium roqueforti, Pencilium cyclopium, Aspergillus tubingensis, Candida cylindracea, Thermomyces lanuginosus, Mucor javanicus, Candida antarctica, Chromobacterium viscosum, Pseudomanas fluorescens, Pseudomonas nitroreducans, Chromobacterium viscosum, Bacillus subtilis,* mutants and combinations thereof.

Preferably, the conversion agent is present in the foodstuff. More preferably, the conversion agent is present in an inactive form or in a denatured form in the foodstuff.

In one aspect of the present invention the at least one functional ingredient may be generated from the at least one constituent of the food material by two or more conversion agents. The at least one constituent may be contacted with the two or more conversion agents at the same time or in series or a combination thereof.

Preferably, the at least one constituent of the food material is selected from esters, monoglycerides, diglycerides, triglycerides, fats, including lard, tallow and butter fat; fatty acids, fatty acid esters, waxes, wax esters, oils including oils extracted from or derived from palm oil, sunflower oil, soya bean oil, safflower oil, cotton seed oil, ground nut oil, corn oil, olive oil, peanut oil, coconut oil and rape seed oil, proteins, amino acids, protein hydrolysates, peptides (partly hydrolysed protein), a constituent comprising a hydroxy group (—OH), polyvalent alcohols, including glycerol; water, ethanol, sugars including sucrose, fructose, glucose (dextrose), lactose, and galactose; dextrins including maltodextrin, sorbitol, mannitol, fruit acids and hydroxy acids including citric acid, tartaric acid, lactic acid and ascorbic acid; proteins, amino acids, protein hydrolysates, peptides (partly hydrolysed protein); mixtures and derivatives thereof.

Preferably, the at least one constituent of the food material is in liquid form.

The term "triglyceride" preferably means a triester of an alcohol, preferably glycerol, and a fatty acid. More preferably the triglyceride fatty acid is a triester of an alcohol, preferably glycerol, and a C4 to C24 fatty acid. Preferably the triglyceride fatty acid has an iodine value of from 0 to 125, preferably from 0 to 60.

Preferably, the triglyceride is selected from triglycerides having a fatty acid chain length of no greater than 14 carbons, triglycerides having a fatty acid chain length of from 4 to 14 carbons, triglycerides having a fatty acid chain length of from 6 to 14 carbons, triglycerides having a fatty acid chain length of from 8 to 14 carbons, triglycerides having a fatty acid chain length of from 10 to 14 carbons, triglycerides having a fatty acid chain length of 12 carbons, triglycerides having a fatty acid chain length of from 16 to 24 carbons, triglycerides having a fatty acid chain length of from 16 to 22 carbons, triglycerides having a fatty acid chain length of from 18 to 22 carbons, triglycerides having a fatty acid chain length of from 18 to 20 carbons, mixtures and derivatives thereof.

Preferably, the functional ingredient is generated from at least two constituents of the food material. In this aspect at least two constituents of the foodstuff may interact and/or react and/or combine together to generate at least one functional ingredient. Preferably, the functional ingredient is generated from a first constituent and a second constituent of the food material.

Preferably, the first constituent and the second constituent are constituents of the foodstuff. In this aspect, the functional ingredient is generated from a first constituent and a second constituent of the food material and the first constituent and second constituent are also present in the foodstuff. Thus the functional ingredient may be generated from constituents/ingredients of the food material which are only partially used to generate the functional ingredient. The remainder of the constituents/ingredients may be present in the foodstuff.

In a preferred aspect of the present invention the first constituent of the food material/foodstuff is hydrophobic and/or lipophilic.

Preferably, the first constituent of the food material/foodstuff is selected from esters, monoglycerides, diglycerides, triglycerides, fats, including lard, tallow and butter fat; fatty acids, fatty acid esters, waxes, wax esters, oils including oils extracted from or derived from palm oil, sunflower oil, soya bean oil, safflower oil, cotton seed oil, ground nut oil, corn oil, olive oil, peanut oil, coconut oil and rape seed oil; derivatives and mixtures thereof. More preferably, the first constituent of the food material/foodstuff comprises or is an ester or a triglyceride.

The term "triglyceride" preferably has the meaning defined above.

Preferably, the triglyceride of the first constituent is selected from triglycerides having a fatty acid chain length of no greater than 14 carbons, triglycerides having a fatty acid chain length of from 4 to 14 carbons, triglycerides having a fatty acid chain length of from 6 to 14 carbons, triglycerides having a fatty acid chain length of from 8 to 14 carbons, triglycerides having a fatty acid chain length of from 10 to 14 carbons, triglycerides having a fatty acid chain length of 12 carbons, triglycerides having a fatty acid chain length of from 16 to 24 carbons, triglycerides having a fatty acid chain length of from 16 to 22 carbons, triglycerides having a fatty acid chain length of from 18 to 22 carbons, triglycerides having a fatty acid chain length of from 18 to 20 carbons, mixtures and derivatives thereof.

Preferably, the first constituent of the food material/foodstuff is in liquid form.

In a preferred aspect of the present invention the second constituent of the food material/foodstuff is hydrophilic.

In a preferred embodiment, the second constituent of the food material/foodstuff may be selected from proteins, amino acids, protein hydrolysates, peptides (partly hydrolysed protein), mixtures and derivatives thereof.

In this aspect, wherein the first constituent of the food material/foodstuff is preferably a fatty acid, it is possible to esterify the free amino groups in the proteinatious second constituent with fatty acid from the first constituent. In this manner, it is possible to produce protein fatty acid condensate. Alternatively, the present invention provides a process; in which the first constituent of the food material/foodstuff is selected from esters, monoglycerides, diglycerides, triglycerides, fats (including tallow and lard), fatty acid esters, and oils (including palm oil, and soya oil rape seed oil), and in which the second constituent is proteinatious; wherein the first constituent interesterifies with the proteinatious second constituent. In these manners, it is possible to produce protein fatty acid condensate.

Protein fatty acid condensate has very good surface active properties. Protein fatty acid condensate is known within the cosmetic and textile industry (see Herstellung und Anvendungmöglichkeiten von Eiweiss-Fettsäurekondensaten. Andreas Sander, Eberhard Eilers, Andrea Heilmann, Edith von Kreis. Fett/lipid 99 (1997) Nr. 4, 115-120). This condensate is normally produced by a reaction between protein and fatty acid chloride as disclosed in Sander et al. However, enzymatic processes for the production of protein fatty acid condensate from protein and fatty acid is known (WO 97/14713). The present applicants have identified that by utilising the commonly occurring constituents of food material, an emulsifier in the form of protein fatty acid condensate may be provided.

This is particularly advantageous because protein forms part of many types of food and is the basic material in many products, for example meat products. In the food industry protein is also often used as a purified protein isolated from milk and plants, such as soya, wheat, rice. Protein is also prepared and is available in hydrolysed form, i.e. protein hydrolysate, peptides or amino acids.

In the above aspect of the present invention, wherein a protein fatty acid condensate is formed, it is important to contact the first constituent and the second constituent with the conversion agent under conditions of agitation. Moreover, it is important to contact these constituents under conditions of controlled water activity. Both of these preferred features will assist in obtaining a maximum conversion rate of first constituents/second constituent to functional ingredient.

Preferably, the second constituent of the food material/foodstuff is selected from a constituent comprising a hydroxy group (—OH), polyvalent alcohols, including glycerol; water, ethanol, sugars including sucrose, fructose, glucose (dextrose), lactose, and galactose; dextrins including maltodextrin, sorbitol, mannitol, fruit acids and hydroxy acids including citric acid, tartaric acid, lactic acid and ascorbic acid; mixtures and derivatives thereof. More preferably, the second constituent of the food material/foodstuff is glycerol.

In a further preferred embodiment, the first constituent of the food material/foodstuff is an ester, preferably a triglyceride and the second constituent of the food material/foodstuff is a constituent comprising a hydroxy group (—OH). Preferably, the first constituent of the food material/foodstuff is a triglyceride. Preferably, the second constituent of the food material/foodstuff is an alcohol, more preferably a polyvalent alcohol, yet more preferably glycerol.

Preferably, the second constituent of the food material/foodstuff is in liquid form.

In a highly preferred embodiment, the first constituent of the food material/foodstuff is a constituent comprising at least two ester groups, preferably a triester, more preferably a triglyceride and the second constituent of the food material/foodstuff is a sugar or a sugar alcohol. In this highly preferred aspect the first constituent and the second constituent may interact on contact with the a conversion agent to generate an ester derived from the first constituent wherein the ester has a lower degree of esterification than the first constituent, and a sugar ester. This is extremely advantageous because the ester may act as a functional ingredient, such as an emulsifier, and the sugar ester may also act as a functional ingredient, such as an emulsifier or an anti-oxidant. Thus, two functional ingredients may be generated from two constituents of the food material/foodstuff by a conversion agent.

In the above highly preferred aspect the second constituent is preferably ascorbic acid. Ascorbic acid ester is an antioxidant.

Thus, in a further broad aspect of the present invention there is provided a foodstuff prepared from a food material, wherein the foodstuff comprises at least two functional ingredients, and wherein the at least two functional ingredients have been generated from a first constituent of the food material and a second constituent of the food material by a conversion agent. Preferably, the first constituent is a constituent comprising at least two ester groups, preferably a triester, more preferably a triglyceride. Preferably, the second constituent is a sugar or a sugar alcohol, more preferably ascorbic acid.

In a preferred aspect, the first constituent of the food material/foodstuff and the first constituent of the food material/foodstuff are in liquid form.

In a further preferred aspect, the food material/foodstuff further comprises greater than two constituents. Preferably, the food material/foodstuff further comprises a third constituent. The third constituent may be selected from the constituents listed above in respect of the first and second constituents. Preferably, the third constituent is selected from a constituent comprising a hydroxy group (—OH), polyvalent alcohols, including glycerol; water, ethanol, sugars including sucrose, fructose, glucose (dextrose), lactose, is and galactose; dextrins including maltodextrin, sorbitol, mannitol, fruit acids and hydroxy acids including citric acid, tartaric acid, lactic acid and ascorbic acid; mixtures and derivatives thereof.

Preferably, the third constituent of the food material/foodstuff is selected from sugars including sucrose, fructose, glucose (dextrose), lactose, and galactose; dextrins including maltodextrin, sorbitol, mannitol, fruit acids and hydroxy acids including citric acid, tartaric acid, lactic acid and ascorbic acid; mixtures and derivatives thereof.

In a highly preferred aspect of the present invention the second constituent of the food material/foodstuff is selected from polyvalent alcohols, preferably glycerol, and the third constituent of the food material/foodstuff is selected from sugars. In an alternative highly preferred aspect of the present invention the second constituent of the food material/foodstuff is selected from polyvalent alcohols, preferably glycerol, and the third constituent of the food material/foodstuff is selected from proteins, peptides and amino acids. These preferred aspects are advantageous because the third constituent may be soluble in the second constituent. Thus, the second constituent can readily react with the third constituent. Moreover, when the first constituent of the food material/foodstuff is in liquid form, the second constituent and/or the third constituent can readily react with the first constituent.

The provision of one or more constituents in liquid form as described above may significantly increase the reaction velocity of the generation of the least one functional ingredient.

The conversion agent may be contacted with the all of the food material or a portion thereof. In the former case, a portion of the food material is contacted with the conversion agent and the contacted material is subsequently contacted with the further constituents of the food material. In the latter case, a portion of the food material may be removed from the total amount of food material. After contacting the conversion agent with the portion of food material, the portion may be returned to the remainder of food material. The portion of the food material may comprises from 0.1 to 10 wt % of the total food material, preferably from 0.1 to 5 wt % of the total food material, preferably from 0.1 to 2 wt % of the total food material, more preferably from 0.5 to 1 wt % of the total food material.

An Example of a portion of the food material being contacted with the conversion agent and the contacted material subsequently being contacted with the further constituents of the food material is exemplified in FIG. 1 (Flow diagram for in situ production of emulsifier). FIG. 1 illustrated the contact of an enzyme with an oil/fat to provide a composition comprising an emulsifier. The enzyme present in the contacted food material is then inactivated with heat. The emulsifier containing foodstuff is then mixed with a fat phase and a water phase and fed to tube chiller to provide a water-in-oil margarine.

The conversion agent may be contacted with a carrier prior to contact with the food material. Preferably, the carrier is a constituent of the food material. Preferably, the carrier is a first constituent or a second constituent of the food material as defined above. More preferably, the carrier is glycerol.

The conversion agent may be contacted with the food material under supercritical conditions. In this aspect the conversion agent may be contacted with the food material in a carbon dioxide solvent. Preferably, the carbon dioxide solvent comprises a mixture of carbon dioxide and an alcohol.

Preferably, the functional ingredient of the present invention is generated by a reaction selected from alcoholysis, preferably glycerolysis, hydrolysis, interesterification, and combinations thereof. More preferably the functional ingredient is generated by a alcoholysis reaction, preferably a glycerolysis reaction.

Preferably, the functional ingredient comprises less than 5 wt % of the foodstuff.

Preferably, the functional ingredient comprises from 0.01 to 4 wt % of the foodstuff.

Preferably, the functional ingredient comprises from 0.01 to 2 wt % of the foodstuff.

Preferably, the functional ingredient comprises from 0.01 to 1 wt % of the foodstuff.

Preferably, the functional ingredient comprises from 0.01 to 0.5 wt % of the foodstuff.

Preferably, the functional ingredient comprises from 0.01 to 0.3 wt % of the foodstuff.

Preferably, the at least one functional ingredient comprises or is a functional ingredient selected from emulsifiers, hydrocolloids, preservatives, antioxidants, colourings and flavourings. More preferably, the at least one functional ingredient comprises or is an emulsifier. In this aspect, preferably the emulsifier comprises from 0.1 to 0.3 wt % of the foodstuff.

The emulsifier may comprise or may be selected from monoglycerides, diglycerides, derivatives and mixtures thereof.

The antioxidant may be anhydrofructose. In this aspect, the at least one constituent is preferably a glucan, more preferably a starch. In this aspect, the conversion agent is preferably a lyase enzyme, yet more preferably an enzyme as described in and/or as claimed in International Patent Application No. PCT/IB98/00708, filed 6 May 1998.

In one aspect of the present invention the at least one functional ingredient is other than an antioxidant. In a further aspect of the present invention the foodstuff does not contain an antioxidant generated in accordance with the present invention. In a further aspect of the present invention the foodstuff does not contain an antioxidant.

In a farther aspect of the present invention the food material and/or the food material contacted with the conversion agent and/or the conversion material is substantially free of water. In this aspect, the creation of free fatty acids and there presence in the foodstuff may be reduced or avoided when the food material is contacted with the conversion agent.

An example of the is aspect of the invention is provided wherein a lipase carried in glycerol, preferably in a glycerol/sugar mixture is contacted with a triglyceride. In this aspect advantageous mono-diglycerides and, preferable, sugar esters are generated as functional ingredients.

$$\text{Triglyceride} + \text{glycerol} \xrightarrow{\text{lipase}} \text{mono-diglyceride and triglyceride}$$

or:

$$\text{Triglyceride} + \text{glycerol}/\text{sugar} \xrightarrow{\text{lipase}} \text{mono-diglyceride and triglyceride} + \text{sugar esters}$$

A person skilled in the art will appreciate that the at least one constituent of the food material from which the functional ingredient is generated may be selected to provide a required functional ingredient. Thus in the above aspect wherein the functional ingredient is an emulsifier, preferably an emulsifier selected from monoglycerides, diglycerides, derivatives and mixtures thereof, the at least one constituent may be, for example, a triglyceride and a polyvalent alcohol.

In a preferred aspect the present invention provides foodstuff as defined above wherein the foodstuff is selected from baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including coffee cream, whipped cream, custard cream, milk drinks and yoghurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions, sauces and mayonnaise.

In one aspect of the present invention the foodstuff is a foodstuff other than mayonnaise.

The claims of the present application are to be construed to include each of the foodstuffs listed above.

In a preferred embodiment the foodstuff of the present invention is a spread, preferably a margarine.

Thus in a preferred aspect the present invention provides a margarine prepared from a food material, wherein the foodstuff comprises at least one functional ingredient, and wherein the at least one functional ingredient has been generated from at least one constituent of the food material by a conversion agent.

In a further preferred embodiment the foodstuff comprises greater than 30 wt % fat (i.e. triglycerides), more preferably greater than 40 wt % fat, yet more preferably greater than 50 wt % fat.

The foodstuff may comprise an emulsion of oil and water. The emulsion may be an oil-in-water emulsion. The emulsion may be an water-in-oil emulsion.

The invention will now be described, by way of example only, with reference to the following examples.

EXAMPLES

Example 1

Full-fat Table Margarine

Full-fat table margarine is used for spreading on bread and household baking.

Each of fat blends A, B and C listed in Table 1 were treated with lipase as follows. 1 part of the fat blend is heated to 50° C. during stirring 0.2 part of lipase (obtained from *Aspergillus tubingensis*) dispersed in glycerol is added. The fat blend is reacted for 12 hours at 50° C. and then shortly heated to 100° C. to denature the enzyme.

TABLE 1

|  | A | B | C |
|---|---|---|---|
| Fat blends |  |  |  |
| Margarine used at approx. | 5-10° C. | 20-25° C. | 25-30° C. |
| Soya 41° C. | 20 | — | — |
| Soya 35° C. | 20 | — | — |
| Soya oil | 60 | 25 | 20 |
| Palm 43° C. | — | 25 | 30 |
| Palm oil | — | 50 | 50 |
| SFC* values of fat blends (IUPAC method) |  |  |  |
| 5° C. | 34 | 47 | 54 |
| 10° C. | 28 | 45 | 50 |
| 20° C. | 14 | 26 | 30 |
| 30° C. | 3 | 10 | 12 |
| 35° C. | 0 | 5 | 7 |
| 40° C. | 0 | 1 | 2 |
| Slip melting point ° C. (AOCS 3-25 method) | 26.3 | 36.9 | 36.8 |

*Solid fat content

The treated fat blends were then processed in accordance with the following steps to prepare a recipe shown in Table 2
1. Blend the water phase ingredients. (If required, pasteurise the water phase by heating to approx. 80° C.). Adjust pH with Ferment Flavouring 4646.
2. Melt the fat phase, and temper to approx. 40-45° C. Add the β-carotene.
3. Add the flavouring.
4. Add the water phase to the fat phase, stirring continuously.
5. Cool in a tube chiller (normal capacity, normal cooling) to an outlet temp of 8-10° C.

TABLE 2

| Water phase: |  |
|---|---|
| Water | 16.0% |
| Skimmed milk powder or whey powder | 1.0% |
| Salt | 1.0% |
| pH 5.0-5.5 with Ferment Flavouring 4646* |  |
| Fat phase: |  |
| Lipase treated fat | 1.2% |
| Soya lecithin | 0.2% |
| β-carotene | 4 ppm |
| Fat blend | 80.6% |
| Butter Flavouring 3559** | 0.01% |

*Ferment Flavouring 4646 - a nature-identical, water-soluble flavouring which ensures a good, lactic and fermented taste. Used for direct acidification of the water phase to ensure the taste similar to that obtained by microbial fermentation of the milk
**Butter Flavouring 3559 - a nature-identical, fat-soluble flavouring which provides a rich, fermented butter taste.

The fat contacted with lipase generated an emulsifier, a functional ingredient which is important in the preparation of margarine. Each of the margarines prepared from fat blends A, B and C was visually inspected and found to substantially identical in appearance to conventionally prepared margarine. No separation of the oil and water phases was observed. Each of the margarines prepared from fat blends A, B and C was also spread on bread and tasted. The organoleptic properties of each margarine was pleasant and were felt by the taster to be substantially identical to those of conventionally prepared margarine.

Example 2

60% Fat Spread with Protein

60% fat spread with protein is used for spreading on bread and open pan frying instead of fill-fat products.

Each of fat blends A and B listed in Table 3 were treated with lipase as follows. 1 part of the fat blend is heated to 50° C. during stirring 0.2 part of lipase (obtained from *Rhizopus arrhizus*) dispersed in glycerol is added. The fat blend is reacted for 12 hours at 50° C. and then shortly heated to 100° C. to denature the enzyme.

TABLE 3

|  | A | B |
|---|---|---|
| Fat blends |  |  |
| Spread used at approx. | 5-10° C. | 20-25° C. |
| Soya 41° C. | 25 | 20 |
| Soya 35° C. | — | 45 |
| Soya oil | 75 | 35 |
| SFC values of fat blends (IUPAC method) |  |  |
| 5° C. | 23 | 48 |
| 10° C. | 19 | 46 |
| 20° C. | 9 | 28 |
| 30° C. | 2 | 8 |
| 35° C. | 0 | 2 |
| 40° C. | 0 | 0 |
| Slip melting point ° C. (AOCS 3-25 method) | 26.6 | 31.7 |

The treated fat blends were then processed in accordance with the following steps to prepare a recipe shown in Table 4
1. Blend the water phase ingredients. (If required, pasteurise the water phase by heating to approx. 80° C.). Adjust pH.
2. Melt the fat phase, and temper to approx. 40-45° C. Add the β-carotene.
3. Add the flavouring.
4. Add the water phase to the fat phase, stirring vigorously.
5. Crystallise and knead vigorously in a tube chiller (80% of normal capacity, $NH_3$ –15° C., 2 tubes) to an outlet temperature of 8-10° C.

TABLE 4

| Water phase at pH 5.5: |  |
|---|---|
| Water | 37.9% |
| Whey powder | 1.0% |
| Salt | 1.0% |
| K-sorbate | 0.1% |
| Fat phase: |  |
| Lipase treated fat | 1.4% |
| β-carotene | 4 ppm |
| Fat blend | 58.6% |
| Butter Flavouring 3559 | 0.01% |

The fat contacted with lipase generated an emulsifier. Both of the margarines prepared from fat blends A and B was visually inspected and found to substantially identical in appearance to conventionally prepared margarine. No separation of the oil and water phases was observed. Both of the margarines prepared from fat blends A and B was also spread on bread and tasted. The organoleptic properties of each margarine was pleasant and were felt by the taster to be substantially identical to those of conventionally prepared margarine.

Example 3

40% Fat Spread with Whey Powder

Fat blend A listed in Table 3 above was treated with lipase as follows. 1 part of the fat blend is heated to 50° C. during stirring 0.2 part of lipase (obtained from *Candida rugosa*) dispersed in glycerol is added. The fat blend is reacted for 12 hours at 50° C. and then shortly heated to 100° C. to denature the enzyme and used for 40% fat spread production. The spread had a composition shown in Table 5 below.

TABLE 5

| Water phase at pH 5.5 | |
|---|---|
| Water | 55.16% |
| Salt | 1.2% |
| K-sorbate | 0.1% |
| Whey powder | 1.0% |
| GRINDSTED ™ Pectin LFS 100 | 1.0% |
| Fat phase | |
| Fat blend 25 parts soya 41° 75 parts liquid oil | 39.5% |
| β-carotene | 4 ppm |
| Butter Flavouring 2873 | 0.01% |
| Butter Flavouring 3507 | 0.01% |
| Lipase treated fat | 2.0% |

The fat contacted with lipase generated an emulsifier. The low-fat spread was stable and had good water dispersion. Sensory evaluation of the sample showed that they had a very good flavour release and colour.

Example 4

Filling Cream

Each of fat blends A and B listed in Table 3 above were treated with lipase as follows. 1 part of the fat blend is heated to 45° C. during stirring 0.2 part of lipase (obtained from *Rhizopus delemar*) dispersed in glycerol is added. The fat blend is reacted for 12 hours at 45° C. and then shortly heated to 100° C. to denature the enzyme and used for filling cream production.

Filling cream was made in a ice cream freezer with monopump (capacity 27 kg/hr). Nitrogen blown in after the pump and before the cooling cylinder. Outlet temperature: 15-17° C.

The filling cream spread had a composition shown in Table 6 below.

TABLE 6

| Water phase | |
|---|---|
| Water | 12.5% |
| GRINDSTED ™ Pectin LFS 100 | 0.5% |
| SMP | 8.0% |
| Sucrose | 9.9% |
| Invert sugar | 9.0% |
| Sorbitol 70% | 8.0% |
| Glucose syrup | 14.0% |

TABLE 6-continued

| Glycerol | 7.0% |
|---|---|
| K-sorbate | 0.1% |
| Fat phase | |
| Lipase treated fat | 3.0% |
| Lecithin | 0.4% |
| Fat blend (100% coconut 31° C.) | 27.6% |
| Butter flavouring 2598 | 0.03% |

The fat contacted with lipase generated an emulsifier. The filling cream was smooth with good flavour release. Specific gravity of the cream: 0.8 g/ml.

Example 5

Ice Cream 1 part of soya fat 41° is heated to 45° C. during stirring 0.2 part of lipase (obtained from *Aspergillus niger*) dispersed in glycerol is added. The fat blend is reacted for 12 hours at 45° C. and then shortly heated to 100° C. to denature the enzyme and used for ice cream production.

The treated fat was then processed in accordance with the following steps to prepare a recipes shown in Table 7

1. Heat all liquid ingredients to approx. 40° C.
2. Add dry ingredients. (stabiliser blend is mixed with sugar before addition)
3. If butter/butter oil or veg. fat is used it must be melted separately and added to the mix at 40° C., or via a static mixer at the entrance to the homogeniser by means of a dosing pump.
4. Pasteurise at 80-85° C./20-40 seconds
5. Homogenise at 80° C. (190 bar for recipe 1 and 175 bar for recipe 2)
6. Cool to ageing temperature, 4° C.
7. Freeze in continues freezer to desired overrun (100% recommended)
8. Harden in tunnel at −40° C.
9. Store below −25° C.

TABLE 7

| Recipe | 1 Milk fat | 2 Veg. fat |
|---|---|---|
| Dairy cream, 38% | 23.65 | |
| Skimmed milk | 53.30 | |
| Skimmed milk powder | 4.90 | 11.30 |
| Vegetable fat (HCO) | | 8.00 |
| Sugar | 12.00 | 12.00 |
| Glucose syrup, DE 42, 75% TS | 5.25 | 5.25 |
| Stabiliser blend | 0.2 | 0.2 |
| Lipase treated fat | 0.6 | 0.6 |
| Grindsted Flavouring 2976 | 0.1 | 0.1 |
| Colour | + | + |
| Water | | 62.55 |

The fat contacted with lipase generated an emulsifier. Ice cream of both recipes had a good taste and excellent creamy mouthfeel.

Example 6

Margarine

In a vessel 0.6 part of sun flower oil and 0.4 part of palm oil and 0.15 part of lipase from *Rhizopus arrhizus* dissolved glycerol/water is added. The reaction is continued for 20 hours at 45° C. and then shortly treated by 100° C. in order to inactivate the enzyme.

Two recipes were prepared. These recipes are shown in Table 8 below. Recipe 1 was in accordance with a prior art method—a previously prepared mono/diglyceride emulsifier (DIMODAN® CP available from Danisco Ingredients, Denmark) was added. Recipe 2 was in accordance with the present invention. In recipe 2, 1.7% of the fat phase was provided by the above lipase treated fat. The lipase treated fat was added to the fat blend for margarine production and the margarine is produced by standard procedures for margarine production.

TABLE 8

| Recipe | 1 | 2 |
|---|---|---|
| WATER PHASE | | |
| Water | 480 | 480 |
| Salt | 30 | 30 |
| Skim Milk Powder | 30 | 30 |
| Potassium Sorbate | 3 | 3 |
| EDTA | 0.45 | 0.45 |
| pH | 5.5 | 5.5 |
| FAT PHASE | | |
| Soya 41° | 490 | 481 |
| Soya 35° | 490 | 481 |
| Soya oil | 1471 | 1444 |
| DIMODAN ® CP | 6.0 | — |
| Lipase | — | 51.0 |
| PPM β-carotene | 0.5 | 0.5 |
| Flavourings | 0.6 | 0.6 |

The fat contacted with lipase generated an emulsifier. The margarine in accordance with the present invention was visually inspected and found to substantially identical in appearance to the conventionally prepared margarine. No separation of the oil and water phases was observed. The margarine in accordance with the present invention was also spread on bread and tasted. The organoleptic properties of the margarine was pleasant and were felt by the taster to be substantially identical to those of the conventionally prepared margarine.

Example 7

Margarine

In a vessel 1 part of palm oil and 0.15 part of esterase from *Candida* dissolved in sugar (sucrose)/water is added. The reaction is continued for 20 hours at 55° C. and then shortly treated by 100° C. in order to inactivate the enzyme.

1% of this reaction mixture is added to a fat blend for margarine production and the margarine is produced by standard procedures for margarine production.

The reaction mixture gives good water in oil emulsification properties.

Example 8

Margarine

In a vessel 1 part of palm oil and 0.15 part of lipase from *Candida* dissolved citric acid/glycerol/water is added. The reaction is continued for 20 hours at 55° C. and then shortly treated by 100° C. in order to inactivate the enzyme.

1% of this reaction mixture is added to a fat blend for margarine production and the margarine is produced by standard procedures for margarine production.

The reaction mixture gives good water in oil emulsification and also contributes to reduce spattering when the margarine is used for frying.

Example 9

Margarine

In a vessel 1 part of palm oil and 0.05 part of lipase from *Aspergillus niger* dissolved water is added. The reaction is continued for 20 hours at 40° C. and then shortly treated by 100° C. in order to inactivate the enzyme.

1% of this reaction mixture is added to a fat blend for margarine production and the margarine is produced by standard procedures for margarine production.

The reaction mixture gives good water in oil emulsification.

Example 10

Margarine

In a vessel 0.8 part of sun flower oil and 0.2 part of soya protein hydrolysate and 0.05 part of lipase from *Rhizopus arrhizus* is added. The reaction is continued for 2 days at 55° C. during vigorous agitation, and then shortly treated by 100° C. in order to inactivate the enzyme.

2% of this reaction mixture is added to a fat blend for margarine production and the margarine is produced by standard procedures for margarine production.

The reaction mixture gives good water in oil emulsification.

Example 11

Ice Cream

In a vessel 0.6 part of palm oil and 0.4 part of milk protein and 0.05 parts of lipase from *Candida* is added. The reaction is continued for 2 days at 55° C. and then shortly treated by 100° C. in order to inactivate the enzyme.

1% of this reaction mixture is used for ice cream production.

The reaction mixture gives good water in oil emulsification properties and stabilise lipid protein boundaries.

Example 12

Custard Cream

In a vessel 1 part of palm oil and 0.3 part peptides from soya bean protein and 0.05 parts of lipase from *Candida* is added. The reaction is continued for 3 days at 55° C. and then shortly treated by 100° C. in order to inactivate the enzyme.

2% of this reaction mixture is used for the production of custard cream.

The reaction mixture gives good water in oil emulsification and contributes to improved stability and mouth feel.

Example 13

Margarine

In a vessel 0.75 part of soya bean oil, 0.25 part milk protein and 0.05 part of lipase from *Aspergillus niger* is added. The reaction is continued for 3 days at 40° C. and then shortly treated by 100° C. in order to inactivate the enzyme.

2% of this reaction mixture is added to a fat blend for margarine production and the margarine is produced by standard procedures for margarine production.

The reaction mixture gives good water in oil emulsification.

Example 14

Sponge Cake 0.05 parts of sugar is dissolved in 0.15 part of glycerol. To this solution 0.75 part of soya bean oil, and 0.05 part of lipase from *Rhizopus arrhizus* is added. The reaction is continued during stirring for 1 day at 45° C. and then the reaction mixture, comprising a functional ingredient, is shortly treated at 100° C. in order to inactivate the enzyme.

This reaction mixture is used for sponge cake production. The reaction mixture gave good emulsification properties and produced a cake with a stable crumb structure and a good volume.

| Sponge Cake Recipe | |
|---|---|
| Ingredients | Gram |
| Sugar | 208 |
| Wheat Flour | 188 |
| Corn starch | 60 |
| Baking Powder | 14 |
| Egg | 200 |
| Soya oil | 40 |
| Water | 110 |
| Functional ingredient | 30 |

Procedure
Mix all ingredients for 6 min. on a Hobart N50 mixer.
Scale 2×350 g into round sponge cake tins.
Bake 35 min at 180° C.

Example 15

Soft Table Margarine

| Materials | |
|---|---|
| Palm oil: | Palmotex from Aarhus Oil, Denmark |
| Glycerol: | Food grade 99.5% |

-continued

| Materials | |
|---|---|
| Lipase #1920: | Lipase PS "Amano" from *Pseudomonas cepacia*, available from Amano, Japan |
| DIMODAN ® BP: | Distilled monoglyceride from Danisco Ingredients, Denmark |

Palm oil was reacted with at solution of lipase in glycerol according to the following recipe Table 9 and Table 10

TABLE 9

| | | 1 | 2 | 3 | 4 | 5 |
|---|---|---|---|---|---|---|
| Palmotex, palm oil | g | 100 | 100 | 100 | 100 | 100 |
| Glycerol-lipase solution | g | 32 | 21 | 11 | 32 | 11 |

TABLE 10

| Glycerol-lipase solution | | 1 | 2 | 3 | 4 | 5 |
|---|---|---|---|---|---|---|
| Glycerol | | 90 | 90 | 90 | 95 | 95 |
| Lipase #1920, solution in water | 5100 LUT/g | 10 | 10 | 10 | 5 | 5 |

Procedure:

2.5 gram of lipase #1920 was dissolved in 15 ml of water whilst being stirred at ambient temperature. A glycerol-lipase solution was prepared as disclosed in Table 10. The glycerol lipase solutions were added to the palm oil in accordance with the recipes of Table 9 and incubated at 45° C. for 20 hours.

The samples were then heated to 90° C. for 10 minutes and the upper oil phase was isolated. The isolated oil phases were analysed by GLC. The results obtained are given in Table 11.

TABLE 11

| | | 1 | 2 | 3 | 4 | 5 |
|---|---|---|---|---|---|---|
| Glycerol | % | 2.3 | 2.1 | 2 | 2.2 | 1.4 |
| Free fatty acid | % | 5.7 | 4.8 | 4.3 | 3 | 2.4 |
| Monoglyceride | % | 24.5 | 24.6 | 24 | 25 | 19.7 |
| Diglyceride | % | 47.3 | 48 | 47.7 | 48.2 | 47.6 |
| Triglyceride | % | 20.2 | 20.5 | 21.9 | 21.7 | 28.8 |

Table 11 indicates that 20-25% monoglyceride was formed during this enzymatic reaction. These samples were used to prepare a soft table margarine according to the recipe given in Table 12 below

TABLE 12

| | Margarine No. | | | | | | |
|---|---|---|---|---|---|---|---|
| | 1 | 2 | 3 | 4 | 5 | 6 | 7 |
| Water phase | | | | | | | |
| Waterphase | 16 | 16 | 16 | 16 | 16 | 16 | 16 |
| Salt | 1 | 1 | 1 | 1 | 1 | 1 | 1 |
| Skim milk powder | 1 | 1 | 1 | 1 | 1 | 1 | 1 |
| Potassium sorbate | 0.1 | 0.1 | 01 | 0.1 | 0.1 | 0.1 | 0.1 |
| EDTA | 0.015 | 0.015 | 0.015 | 0.015 | 0.015 | 0.015 | 0.015 |
| pH | 5.5 | 5.5 | 5.5 | 5.5 | 5.5 | 5.5 | 5.5 |
| Water phase total | 18.1 | 18.1 | 18.1 | 18.1 | 18.1 | 18.1 | 18.1 |
| Fat phase | | | | | | | |
| Soya, 41° C. | 20 | 20 | 20 | 20 | 20 | 20 | 20 |

TABLE 12-continued

|  | Margarine No. | | | | | | |
|---|---|---|---|---|---|---|---|
|  | 1 | 2 | 3 | 4 | 5 | 6 | 7 |
| Soya, 35° C. | 20 | 20 | 20 | 20 | 20 | 20 | 20 |
| Soya oil | 60 | 60 | 60 | 60 | 60 | 60 | 60 |
| Fat phase total | 81.7 | 81.02 | 81.02 | 81.03 | 81.08 | 80.88 | 81.6 |
| Dimodan BP | 0.2 |  |  |  |  |  |  |
| Sample 1 |  | 0.88 |  |  |  |  |  |
| Sample 2 |  |  | 0.88 |  |  |  |  |
| Sample 3 |  |  |  | 0.87 |  |  |  |
| Sample 4 |  |  |  |  | 0.82 |  |  |
| Sample 5 |  |  |  |  |  | 1.02 |  |
| Soya lecithin |  |  |  |  |  |  | 0.3 |
| β-carotene, ppm | 3 | 3 | 3 | 3 | 3 | 3 | 3 |
| Fat phase total | 81.9 | 81.9 | 81.9 | 81.9 | 81.9 | 81.9 | 81.9 |
| Flavorings: |  |  |  |  |  |  |  |
| Flavouring 2565*, % | 0.01 | 0.01 | 0.01 | 0.01 | 0.01 | 0.01 | 0.01 |
| Flavouring 2712*, % | 0.01 | 0.01 | 0.01 | 0.01 | 0.01 | 0.01 | 0.01 |

*Butter Flavouring 2565 and Butter Flavouring 2712 are available from Danisco Ingredients, Denmark.

Evaluation

Margarine numbers 1 to 7 were evaluated after 4 days storage at 5° C.

Visual:

Margarines 1 to 7 all produced fine and stable margarine.

Margarines 2 to 6 were slightly more firm than 1 and 7.

Organoleptic:

Each of margarines 1 to 7 gave very good melting properties on the tongue.

Microscopy:

Margarines 1, 5, 6 and 7 gave very good dispersions of water particles in the fat phase, with an average diameter of 4-5 μm.

Margarines 2, 3 and 4 also produced a fine dispersion with water particles approx. 5 μm, but a few water particles of 10 μm were observed.

From the experiment with margarine it can be concluded that the enzymatic interesterification of palm oil (Margarine Nos. 1 to 5) can be used to produce margarine which is equal in quality to commercial products. Furthermore, it is shown that these samples can substitute distilled monoglyceride or lecithin for the production of a soft table margarine. The change in firmness observed using interesterified palm oil in place of lecithin can be adjusted by changing the fat composition of the fat phase in the margarine.

Example 16

Puff Pasty Margarine

Materials:
Palm oil:
Palm stearin:       Melting point 55° C.
Palm:               Melting point 43° C.
Rape seed oil:
Glycerol:           Food grade 99.5%
Lipase #1920:       Lipase PS "Amano" from *Pseudomonas cepacia*
DIMODAN ® BP:       Distilled monoglyceride from Danisco Ingredients, Denmark
DIMODAM ® PVP:      Distilled monoglyceride from Danisco Ingredients, Denmark
Flavouring O2986:   Butter flavouring available from Danisco Ingredients, Denmark Palm oil and palm stearin were reacted with at solution of lipase in glycerol according to the following recipe Table 13 and Table 14.

TABLE 13

|  |  | Sample 1 | Sample 2 |
|---|---|---|---|
| Palmotex, palm oil | g | 300 |  |
| Palm stearin | g |  | 200 |
| Glycerol-lipase solution 1 | g | 33 | 22 |

TABLE 14

| Glycerol-lipase solution | | |
|---|---|---|
| Glycerol |  | 90 |
| Lipase #1920, solution in water | 5100 LUT/g | 10 |

Procedure:

2.5 g lipase #1920 were dissolved in 15 ml water during stirring at ambient temperature. Glycerol-lipase solution was made as mentioned in Table 14.

The glycerol-lipase solutions were added to the palm oil or palm stearin as shown in Table 13 and incubated at 45° C. for 20 hours.

The samples were heated to 90° C. for 10 min and the upper oil phase isolated.

TABLE 15

|  |  | Sample 1 | Sample 2 |
|---|---|---|---|
| Glycerol | % | 1.3 | 2.9 |
| Free fatty acid | % | 7.2 | 6.5 |
| Monoglyceride | % | 19.2 | 16.1 |
| Diglyceride | % | 42.3 | 42.9 |
| Triglyceride | % | 29.8 | 31.5 |

Table 15 indicate that 15-20% monoglyceride was formed during this enzymatic reaction.

These samples were used to produce a puff pastry margarine according to the recipe of Table 16.

TABLE 16

|  | Margarine | | | |
|---|---|---|---|---|
|  | 1 | 2 | 3 | 4 |
| Water phase | | | | |
| Water phase | 36.9 | 36.9 | 36.9 | 36.9 |
| Salt | 2 | 2 | 2 | 2 |
| Sugar | 1 | 1 | 1 | 1 |
| Potassium sorbate | 0.1 | 0.1 | 0.1 | 0.1 |
| EDTA | 0.015 | 0.015 | 0.015 | 0.015 |
| pH | 3 | 3 | 3 | 3 |
| Water phase total, % | 40 | 40 | 40 | 40 |
| Fat phase | | | | |
| Palm stearin 55 | 20 | 20 | 20 | 20 |
| Palm 43 | 25 | 25 | 25 | 25 |
| Palm oil | 45 | 45 | 45 | 45 |
| Rape seed oil | 10 | 10 | 10 | 10 |
| Fat total, % | 58.8 | 58.8 | 54.8 | 54.8 |
| Dimodan PVP, % | 1 | | | |
| Dimodan BP, % | | 1 | | |
| Sample 1, % | | | 5 | |
| Sample 2, % | | | | 5 |
| Lecithin, % | 0.2 | 0.2 | 0.2 | 0.2 |
| β-carotene, ppm | | | | |
| Fat phase total, % | 60 | 60 | 60 | 60 |
| Flavouring O2986, % | 0.03 | 0.03 | 0.03 | 0.03 |

Evaluation

Margarines 1 to 4 were evaluated after 2 days storage at 5° C.

Visual

Margarines 1 to 4 all produced fine and stable puff pastry margarine

Margarine 1: Soft plastic

Margarine 2: Soft plastic was more soft than Margarine 1

Margarine 3: Soft plastic slightly more soft than Margarine 1

Margarine 4: Soft plastic better than Margarine 1

Microscopy:

Margarine 1 gave very nice dispersions of water particles in the fat phase,

Margarine 2 and Margarine 3 were evaluated equal fine water particles.

Margarine 4 was evaluated slightly better than 1.

Figure 2:
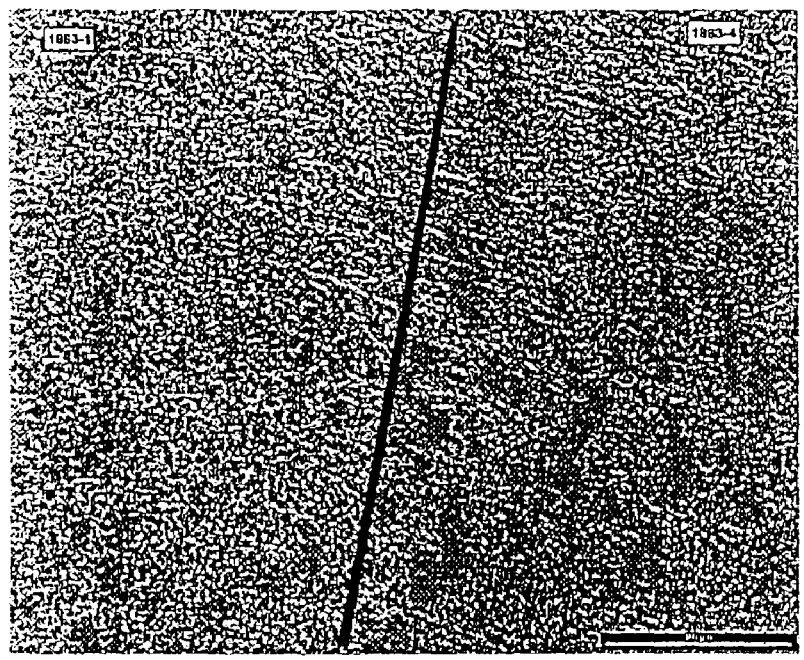
FIG. 2 is a microscopic picture of the margarine samples.
Figure 3:
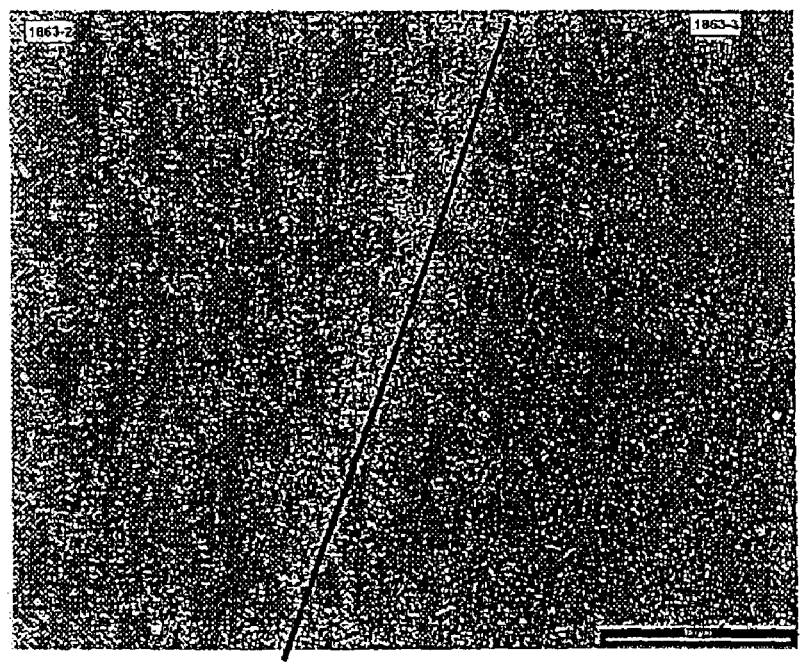
FIG. 3 is a microscopic picture of the margarine samples.

Microscopic pictures of the samples is shown in FIGS. 2 and 3. Margarines 1 to 4 are shown as 1863-1 to 4, respectively.

CONCLUSION

From the experiment with puff pastry margarine it can be concluded that the enzymatic interesterification of palm oil or palm stearin can be used to produce margarine which are fully on level with the quality of commercial products.

It has been shown that these samples made by enzymatic interesterification can substitute distilled monoglyceride for the production of a puff pastry margarine.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A process for preparing a foodstuff which is an edible oil or fat suitable for consumption, wherein the foodstuff comprises a first functional ingredient which is an emulsifier and a second functional ingredient, the process comprising:
   (i) providing a food material containing a triglyceride and a second constituent, wherein the second constituent is glycerol or ascorbic acid;
   (ii) contacting the food material with a lipase, such that an emulsifier is generated by the lipase from the triglyceride and a second functional ingredient is generated from the second constituent;
   (iii) inactivating or denaturing the lipase to provide the foodstuff comprising the emulsifier, the triglyceride, the second functional ingredient and the lipase in an inactive form or a denatured form.

2. A process according to claim 1 wherein the lipase is isolated from a plant, an animal or a micro-organism.

3. A process according to claim 2 wherein the micro-organism is selected from *Aspergillus niger, Rhizopus delemar, Rhizopus arrhizus, Mucor miehei, Pseudomonas* sp., *Candida rugosa, Pencilium roqueforti, Pencilium cyclopium, Aspergillus tubingensis, Candida cylindracea, Thermomyces lanuginosus, Mucor javanicus, Candida antarctica, Chromobacterium viscosum, Pseudomanas fluorescens, Pseudomonas nitroreducans, Chromobacterium viscosum, Bacillus subtilis,* mutants and combinations thereof.

4. A process according to claim 1 wherein the second constituent is glycerol.

5. A process according to claim 1 wherein the foodstuff is selected from w/o emulsions, o/w emulsions, margarine and shortening.

6. A process according to claim 1 wherein the second constituent is ascorbic acid.

7. A process according to claim 1 wherein the emulsifier is selected from monoglycerides, diglycerides, and mixtures thereof.

8. The process according to claim 1, wherein the foodstuff comprises greater than 30 wt % fat.

* * * * *

UNITED STATES PATENT AND TRADEMARK OFFICE
CERTIFICATE OF CORRECTION

PATENT NO. : 7,781,001 B2 Page 1 of 1
APPLICATION NO. : 10/409391
DATED : August 24, 2010
INVENTOR(S) : Jørn Borch Søe It is certified that error appears in the above-identified patent and that said Letters Patent is hereby corrected as shown below:

IN THE SPECIFICATION

Column 5, line 16

The first and second recitation of "Pencilium" should be corrected to --Penicillium--

IN THE CLAIMS

Column 24, claim 3 line 28

The first and second recitation of "Pencilium" should be corrected to --Penicillium--

Signed and Sealed this

Twenty-sixth Day of October, 2010

David J. Kappos
*Director of the United States Patent and Trademark Office*